(12) United States Patent
Zou et al.

(10) Patent No.: US 7,511,189 B2
(45) Date of Patent: *Mar. 31, 2009

(54) DIACYLGLYCEROL ACYLTRANSFERASE GENE FROM PLANTS

(75) Inventors: Jitao Zou, Saskatoon (CA); David C. Taylor, Saskatoon (CA); Yangdou Wei, Saskatoon (CA); Colette C. Jako, Saskatoon (CA)

(73) Assignee: National Research Council of Canada, Ottawa, Ontario (CA)

( * ) Notice: Subject to any disclaimer, the term of this patent is extended or adjusted under 35 U.S.C. 154(b) by 275 days.

This patent is subject to a terminal disclaimer.

(21) Appl. No.: 11/117,005

(22) Filed: Apr. 28, 2005

(65) Prior Publication Data

US 2005/0193446 A1 Sep. 1, 2005

Related U.S. Application Data

(63) Continuation of application No. 09/623,514, filed as application No. PCT/CA99/01202 on Dec. 16, 1999, now Pat. No. 7,015,373.

(60) Provisional application No. 60/112,812, filed on Dec. 17, 1998.

(51) Int. Cl.
*C12N 15/82* (2006.01)
*C12N 5/04* (2006.01)
*A01H 5/10* (2006.01)

(52) U.S. Cl. .................. 800/281; 800/278; 800/294; 800/314

(58) Field of Classification Search ............. 800/278; 435/410, 419, 468
See application file for complete search history.

(56) References Cited

U.S. PATENT DOCUMENTS 7,015,373 B1 * 3/2006 Zou et al. .............. 800/298
2002/0170091 A1 * 11/2002 Lassner et al. ............ 800/281

FOREIGN PATENT DOCUMENTS

WO WO 99 63096 A 12/1999
WO WO 99 67403 A 12/1999
WO WO 00 01713 A 1/2000

OTHER PUBLICATIONS

Bowie et al., (1990, Science 247:1306-10).
McConnell et al., (2001, Nature 411 (6838):709-713).
Wiberg et al., (1994, Phytochemistry 36(3):573-577).
R61u012 Database Entry Ac005917 Accession No. AC005917; Nov. 4, 1998; Lin X. et al.: "*Arabidopsis thaliana* chromosome II section 113 of 255 of the complete sequence" XP002133608 nucleotides 21090-23400-& Lin X. et al.: "Sequence and analysis of chromosome II of *Arabidopsis thaliana*" Nature, vol. 402, 1999, pp. 761-768, XP000877287 London GB.

Cases S. et al.: "Identification of a gene encoding an acyl CoA: diacylglycerol acyltransferase, a key enzyme in triacylglycerol synthesis" Proceedings of the National Academy of Sciences of USA, US, National Academy of Science. Washington, vol. 95, No. 22, Oct. 27, 1998, pp. 13018-13023, XP002122745, ISSN: 0027-8424.

Vesna Katavic et al.: "Alteration of seed fatty acid composition by an ethyl methanesulfonate-induced mutation in *Arabidopsis thaliana* affecting diacylglycerol acyltransferase activity" Plant Physiology, vol. 108, 1995, pp. 399-409, XP002915657.

Empln Database Entry Ath238008 Accession No. AJ238008; Jun. 18, 1999 Zou J. et al.: "The *Arabidopsis thaliana* TAG1 gene encodes for a diacylglycerol acyltransferase" XP002133609.

Zou, Jitao et al.: "The *Arabidopsis thaliana* TAG1 mutant has a mutation in a diacylglycerol acyltransferase gene" Plant J. (1999), 19(6), 645-653, XP002133607.

EMBL database Entry AF155224 Accession No. AF155224; Jun. 30, 1999 Nykiforuk C. L. et al.: "*Brassica napus* putative diacylglycerol cyltransferase (DGAT2) mRNA" XP002133639 & Nykiforuk C.L. et al., "Isolation and sequence analysis of a novel cDNA encoding a putative diacylglycerol acyltransferase from a microspore-derived cell suspension culture of *Brassica napus* L. ev Jet Neuf (Accession No. AF155224) (PGR99-123)." Plant Physiology, vol. 120, No. 4, 1999, pp. 1207-1207, London, GB.

EMBL Database Entry AF164434 Accession No. AF164434; Jul. 26, 1999 Nykiforuk, C. L. et al.: "*Brassica napus* putative diacylglycerol acyltransferase (DGAT1) mRNA" XP002133640 & Nykiforuk C.L. et al.: "Isolation and characterization of a cDNA encoding a second putative diacylglycerol acyltransferase from a microspore-derived cell suspension culture of *Brassica napus* L. ev Jet Neuf (Accession No. AF164434) (PGR99-158)" Plant Physiology, vol. 121, No. 3, 1999, pp. 1053-1053.

Hobbs D. H. et al., "Cloning of a cDNA encoding diacylglycerol acyltransferase from *Arabidopisis thaliana* and its functional expression" FEBS Letters, NL, Elsevier Science Publishers, Amsterdam, vol. 452, No. 3, Jun. 11, 1999, pp. 145-149, WP002122747 ISSN: 0014-5793.

Rounsley et al., *Arabidopsis thaliana* chromosome II BAC F27F23 genomic sequence, GenBank Accession No. AC003058.1, May 16, 1998.

* cited by examiner

*Primary Examiner*—Stuart F. Baum
(74) *Attorney, Agent, or Firm*—TraskBritt

(57) ABSTRACT

The present invention relates to the isolation, purification, characterization and use of the plant diacylglycerol acyltransferase (DGAT) gene and genetic products. The invention includes isolated and purified DGAT DNA and relates to methods of regulating seed oil content, the ratio of diacylglycerol/triacylglycerol proportions in the seed oil, fatty acid synthesis, seed oil acryl composition, seed size/weight and carbon flux into other seed components, using the gene, and to tissues and plants transformed with the gene. The invention also relates to transgenic plants, plant tissues and plant seeds having a genome containing an introduced DNA sequence of the invention, and a method of producing such plants and plant seeds.

9 Claims, 10 Drawing Sheets

(a)

```
AtTAG1  MEILDSAGVTTVTENGGGEFVDLDRLRRRKSRSDSSNGLLLSGSDNNSPS  50
MDGAT   MEDRGGAGSER..............RRRTGSRVSVQG....GSGPKVEE  31
HARGP1  MSDR...GSSR..............RRRTGSRPSSHG....GGGPAAAE  28

AtTAG1  DEVGAPEDVRDRIDSVVNDDAQETANLAGDNNGGGDNNGGGRGGCERGN  100
MDGAT   DEVRDAAVSPLL.......GAGEDAPAPAPAPAHTRDKDERTSVERY...  72
HARGP1  EEVRDAAAGPLV.......GAACDAPAPAP......NKDGDAGVGSCH..  63

AtTAG1  ADATETYRPSVPAHRRARESPLSSDEIEKQSHAGENLCVVELAVERI  150
MDGAT   ....WDLRC.....HRLQDSLFSSDGESNYR.CLNWVVLLLSRL  112
HARGP1  ....WELRC.....HRLQDSLFSSDSGESNYR.CLNWCVVVLDLSVRI  103

AtTAG1  IFENLMKYGWLFRTDFWFSSRSLRD...WELFMC.CLSLSIFPEAAFTEE  196
MDGAT   FEENLKYGILVDP.IQVVSLFLDPYSWPA.PCVILASNEVVAAFQEE  160
HARGP1  FEENLKYGILVDP.IQVVSLFLKDPHSWPA.PCLVIAANVFAVAAFQVE  151

AtTAG1  KLALQKYESEPMVEFLHEITMTELLFPVYVTLRCDSAFLSGVTLMLEC  246
MDGAT   KREAVGAERQMGELLEYANLAILTCEPAAVALLVESITPVGSVFALASY  210
HARGP1  KREAVGAEREQAGELLHYANLALILDCEPAAVVLLVESITPVGSLLALSH  201

AtTAG1  .IVELKLVSYAHTSY.....DIRELANAADK......ANPEVSYYVSL..  282
MDGAT   SIVELKIYSYRDVNLWCRQRRVRAKAVETGKVSGAAAQQAVSYPDNLTY  260
HARGP1  TIVELKLFSYRDVNSWC..RRARKAASAGKKASSAAAPHTVSYPDNLTY  249

AtTAG1  KSLAYFWVAPTLCYQPSFPRSACIRKGMAREQFAKEMIFTGFMGFELEQY  332
MDGAT   RDLYYFFAPTLCYELNEPRSPRIRKREILRRVLEMEFFTQLQVGELQQY  310
HARGP1  RDLYYFFAPTLCYELNEPRSPRIRKREILRRILEMEFFTQLQVGELQQY  299

AtTAG1  INPIVRNSKHPLKGDELYA..IERVLKLSVPNLYVWLCMFYCFFHLWLNI  380
MDGAT   MVPTTQNSMKPFK.DVDYGRIIERLLKLAVPKHLIWLIFFYWFFHSCLNA  359
HARGP1  MVPTTQNSMKPFK.DVDHGRIIERLLKLAVPNHLIWLIFFYWLFHSCLNA  348

AtTAG1  LAELCFGDREFYKDWWNAKSVGDYWRMWNMPVHKWMVRHIYFPCLRSKI  430
MDGAT   VAELIQFGDREFYRDWWNAESVTYWQNMWNMPVHKWCIRHFYKPMLRHGS  409
HARGP1  VAELIQFGDREFYRDWWNAESVTYWQNMWNMPVHKWCIRHFYKPMLRRGS  398

AtTAG1  PKTPAIIIAFLVSAVFHELCIAVFCRMFKLWAFLGIMFQVPLV.FITNYL  479
MDGAT   SKWMARTGVFLTSAFFHEYLVSVPLRMCKLWAFTAMMAQIPLAWIVGREF  459
HARGP1  SKWMARTGVFLASAFFHEYLVSVPLRMCKLWAFTGMMAQIPLAWFVGREF  448

AtTAG1  CEREGSTVGNMIFEFIFCIFGQECVLEYYHD..EMNRKGSMS..  520
MDGAT   QGNYGNAA....VEVTL.IIGQPEAVLMYVHDYYWNYDAPVG.V  498
HARGP1  QGNYGNAA....VELSL.IIGQPEAVLMYVHDYYVENYEAPAAEA  488
```

DIACYLGLYCEROL ACYLTRANSFERASE GENE FROM PLANTS

CROSS-REFERENCE TO RELATED APPLICATIONS

This application is a continuation of U.S. application Ser. No. 09/623,514 filed Mar. 29, 2001 now U.S. Pat. No. 7,015,373, issued on Mar. 21, 2006, which is a national phase entry under 35 U.S.C. § 371 of PCT International Patent Application No. PCT/CA99/01202, filed on Dec. 16, 1999, designating the United States of America, and published, in English, as PCT International Publication No. WO 00/36114 on Jun. 22, 2000, which claims priority to U.S. Provisional Patent Application 60/112,812, filed Dec. 17, 1998, each of the contents of the entirety of which is incorporated by this reference.

TECHNICAL FIELD

This invention relates to plant genes useful for the genetic manipulation of plant characteristics. More specifically, the invention relates to the identification, isolation and introduction of acyl-CoA:diacylglycerol acyltransferase (DGAT) genes useful, for example, for altering the seed oil content, the ratio of diacylglycerol/triacylglycerol proportions in the seed oil, fatty acid synthesis, seed oil acyl composition, seed size/weight and carbon flux into other seed components, in commercial or crop plants.

BACKGROUND OF THE INVENTION

Plant seed oils are major sources of essential polyunsaturated fatty acids for human diets and renewable feedstocks for chemical industries. The enzymes of the fatty acid synthase complex in the plastids of developing seeds are responsible for the biosynthesis of fatty acids that are channeled into the cytosolic acyl-CoA pool to sustain triacylglycerol accumulation. Triacylglycerol (TAG) biosynthesis is located in the endoplasmic reticulum with glycerol-3-phosphate and fatty acyl-CoAs as the primary substrates. There are three acyltransferases involved in the plant storage lipid bioassembly, namely the glycerol-3-phosphate acyltransferase (GPAT, EC 2.3.1.15), the lyso-phosphatidic acid acyltransferase (LPAT, EC 2.3.1.51) and the diacylglycerol acyltransferase (DGAT, EC 2.3.1.20). These three acyltransferases catalyze the stepwise acylation of the glycerol backbone with the final step being the acylation of sn-1,2-diacylglycerol (DAG) by DGAT into the formation of TAGs, a biochemical process generally known as the Kennedy pathway (Stymne and Stobart, 1987).

Among the three ER-based fatty acyl-CoA acyltransferases, only LPAT gene(s) have been cloned from plants (Knutzon et al., 1995, Lassner et al., 1995). Like several other enzymes involved in storage lipid biosynthesis, acyltransferases are intrinsic ER proteins and are extremely difficult to purify. The research on plant DGAT has been largely limited to studies of activity profiles by using the particulate fractions generated by differential centrifugation of seed or microspore-derived embryo homogenates (Weselake et al., 1993). Although partial purification of DGAT from cotyledons of germinating soybean seeds was reported (Kwanyuan and Wilson, 1986), detailed molecular characterization of this enzyme is lacking.

Accordingly, while the Kennedy pathway is known and shows the steps in the biosynthesis of TAGs in plants, there has not been any identification and use of a genetic element that can be used reliably in plants to modify the DGAT step in TAG synthesis and composition in a way that may be exploited commercially.

SUMMARY OF THE INVENTION

An object of the invention is to identify, isolate and clone a genetic element that may be used to modify the natural formation of triacylglycerols in plants in order to increase the yield of commercial plant oils, or to modify their composition to achieve specific commercial improvements of plants and plant products.

Another object of the invention is to identify, isolate and characterize diacylglycerol acyltransferase (DGAT) gene and cDNA sequences from *Arabidopsis* and to utilize these sequences in the genetic manipulation of plants.

Another object of the invention is to provide a vector containing the full-length DGAT cDNA sequence from *Arabidopsis* in a sense orientation under the control of a seed-specific promoter (e.g. napin; See Josefsson et al., 1987; Radke et al., 1988; Voelker et al., 1992), for re-introducing into *Arabidopsis* or for introducing into other plants.

Another object of the invention is to provide a vector containing a genomic fragment from *Arabidopsis* consisting of the full-length DGAT gene under the control of its own 5' upstream regulatory sequences, for re-introducing into *Arabidopsis* or for introducing into other plants.

Another object of the invention is to provide a method to construct a vector containing the full-length DGAT sequence or a significant portion of the DGAT sequence from *Arabidopsis*, in an antisense orientation under control of either a constitutive or a seed-specific promoter, for re-introducing into *Arabidopsis* or for introducing into other plants.

Another object of the invention is to provide a method of modifying *Arabidopsis* and other plants to change their seed oil content.

Another object of the invention is to provide a method of modifying *Arabidopsis* and other plants to change the acyl composition of their seed oil.

Another object of the invention is to provide a method of modifying *Arabidopsis* and other plants to change their average seed weight or size.

According to one aspect of the present invention, there is provided a vector containing isolated and purified deoxyribonucleic acid (cDNA) of SEQ ID NO:1 (pDGATcDNA; ATCC No PTA-989), for introduction of the cDNA in a sense orientation into a plant cell.

As another aspect of the present invention, there is provided a vector containing isolated and purified genomic deoxyribonucleic acid (genomic DNA) of SEQ ID NO:3 (PDGAT gene; ATCC No PTA-988), for introduction of the gene in a sense orientation into a plant cell.

According to yet another object of the invention, there is provided a method for preparing a vector containing SEQ ID NO: 1 or a part thereof, for introduction of the gene or partial gene in an antisense orientation, into a plant cell.

According to yet another object of the invention, there is provided seed of *Arabidopsis thaliana* ecotype Columbia mutant AS11 (ATCC No. PTA-1013) and characterization of its lipid phenotype (Katavic et al., 1995; Zou et al. 1999). The AS II mutant seed line has an insertion mutation at the TAG1 locus on chromosome II, and produces plants exhibiting reduced DGAT activity (FIG. 4) and a reduced TAG/DAG ratio during seed development (Table 1), resulting in an altered seed fatty acyl composition (FIG. 2), reduced oil content (Table 1), and increased seed oil diacylglycerol content during development (FIG. 3) and at maturity (lower TAG/

DAG ratio cf Table 1). The cDNA sequence of the AS11 DGAT is shown in SEQ ID NO:23, the genomic DNA sequence is shown in SEQ ID NO:24 and the translated protein sequence of the AS11 DGAT is shown in SEQ ID NO:25.

The invention also relates to transgenic plants and plant seeds having a genome containing an introduced DNA sequence of SEQ ID NO:1 or SEQ ID NO:3, and a method of producing such plants and plant seeds.

The invention also relates to SEQ ID NO:1 or SEQ ID NO:3, or a part of SEQ ID NO:1 or SEQ ID NO:3, or SEQ ID NO:1 containing an 81 bp insertion (SEQ ID NO: 23) or SEQ ID NO:3 containing a 147 bp insertion (SEQ ID NO:24) such that the deduced amino acid sequence of the encoded protein contains the repeated sequence SHAGLFNLCVVVLIAVNS RLIIENLMK (SEQ ID NO:25) where the spacing and identity of the underlined amino acids are identical or are replaced by conserved substitutions, characterized in that said sequence has been introduced in sense or antisense orientation, and a method of producing such plants and plant seeds.

As will be appreciated by persons skilled in the art, the invention also relates to substantially homologous DNA sequences from plants encoding proteins with deduced amino acid sequences of 25% or greater identity, and 40% or greater similarity, isolated and/or characterized and/or designed by known methods using the sequence information of SEQ ID NO:1 or SEQ ID NO:3 or SEQ ID NO:1 containing an 81 bp insertion (SEQ ID NO:23) such that the deduced amino acid sequence of the encoded protein contains the repeated sequence SHAGLFNLCVVVLIAVNSRLIIENLMK (SEQ ID NO:25) where the spacing and identity of the underlined amino acids are identical or are replaced by conserved substitutions, and to parts of reduced length that are still able to function as inhibitors of gene expression by use in an antisense, co-suppression (Transwitch; Jorgensen and Napoli 1994) or other gene silencing technologies (i.e., RNAi). It will be appreciated by persons skilled in the art that small changes in the identities of nucleotides in a specific gene sequence may result in reduced or enhanced effectiveness of the genes and that, in some applications (i.e., anti-sense, co-suppression or RNAi), partial sequences often work as effectively as full length versions. The ways in which the gene sequence can be varied or shortened are well known to persons skilled in the art, as are ways of testing the effectiveness of the altered genes. All such variations of the genes are therefore claimed as part of the present invention.

Other preferred degrees of identity to the indicated sequences are at least 30%, 40%, 50%, 60%, 70%, 80%, 90% and 95%; and other preferred degrees of similarity are at least 50%, 60%, 70%, 80%, 90% and 95%. The inventors have used a computer program known as MegAlign®, DNAS-TAR® of DNASTAR Inc., 1228 South Park Street, Madison, Wis. 53715, USA, for assessing homology. This program is based on the Clustal V algorithm (Higgins and Sharp (1998): A package for performing multiple sequence alignment on a microcomputer; GENE 73:237-244). For each gap introduced in the alignment, the program deducts a penalty from the score. A higher gap penalty suppresses gapping; a lower value promotes it. The program also assesses penalties based on the length of the gap. The more residues the gap spans, the greater the penalty. The program deducts these penalties from the overall score of the alignment.

Stated more generally, the present invention relates to the isolation, purification and characterization of a diacylglycerol acyltransferase (DGAT) gene from the Brassicaceae (specifically *Arabidopsis thaliana*) and demonstrates its utility in regulating fatty acid synthesis, seed oil content, diacylglycerol/triacylglycerol ratios and seed size/weight. Until now, no concrete data is available on the gene structure of plant DGATs, or their utility in altering oil content or composition through genetic manipulation.

When considering altered oil contents or compositions, results from averages of statistically-significant numbers of plants or seeds according to the invention are best compared with results from averages of statistically-significant numbers of untransformed (control) plants or seeds of the same genotype grown under identical conditions at the same time. This allows for the variability of individual plants of the same genotype, particularly when such plants are grown under different conditions. The actual number of plants or seeds used to form the required average may vary, but should be enough to provide a generally constant average whenever such number is selected. Generally, the number should be at least 10, and is more preferably at least 20, 30, 50 or 100.

The DGAT gene was cloned, characterized and authenticated from *Arabidopsis* by: (1) selection and characterization of plant ESTs sharing some homology to mammalian acyl-CoA: cholesterol acyltransferases; (2) the functional expression of a full-length cDNA in yeast; (3) the characterization and isolation of the DGAT (TAG 1) gene from *Arabidopsis* mutant AS11 containing an insertion mutation in the DGAT gene and a seed oil phenotype which consists of an altered DAG/TAG ratio, and an altered oil content and acyl composition; (4) complementation of the AS11 mutant by insertion of the DGAT cDNA sequence to restore a wild-type fatty acid composition; (5) the over-expression of the DGAT cDNA in wild-type *A. thaliana* transgenic plants which produce seeds with an increased oil content, increased average seed weight and altered seed oil acyl composition.

The *A. thaliana* DGAT structure is significantly homologous (over 40% identical over a region of more than 400 amino acids) to its mammalian counterparts, and is highly homologous to subsequently reported putative *B. napus* DGATs at both the nucleotide (92%) and the deduced amino acid (90%) levels (Nikyiforuk et al, 1999; GenBank/EMBL Accession No AF155224; AF164434).

The DGAT of the current invention is useful in manipulating DGAT activity, and triacylglycerol bioassembly in plants. For example, by transforming plants with a construct containing the DGAT gene in a sense orientation, under the control of a tissue-specific promoter (e.g. seed-specific promoter napin), the expression of DGAT and accumulation of seed oil can be enhanced or the acyl composition of the seed oil altered. Yet another example would be to express the DGAT cDNA under the control of a constitutive promoter (e.g. 35S (Datla et al., 1993)) to increase the TAG content of vegetative tissues (leaves, roots, stems). This may have particular advantages for altering the starch/oil ratio in root crops.

Alternatively, DGAT expression can be silenced to some degree by anti-sense or co-suppression (Transwitch) phenomena (De Lange et al., 1995; Mol et al., 1990; Jorgensen and Napoli, 1994; Kinney, 1995; Vaucheret et al, 1998; Taylor, 1998). For example, silencing DGAT in a seed specific manner may result in a reduction in TAG accumulation. This could have applications in reducing the oil content in seed barley to enhance stability during storage. As a second example, seed-specific silencing may lead to a relatively high accumulation of DAG or an increase in the DAG/TAG ratio in the developing or mature seed. As yet another example, the expression of the mutated DGAT gene which results in a 27 amino acid repeat insertion in the mutant DGAT protein (See FIG. 5a) can be used to alter the DAG/TAG ratio in developing and mature seed. Such manipulations can lead to edible seed oils produced naturally in the plant, containing enhanced relative levels of DAG/reduced levels of TAG (See FIG. 3;

Table 1) to act as all-natural emulsifiers in the food and confections industries, or to enhance the nutritional/health profile of vegetable oils as functional foods (e.g. as cooking oils, stir fry oils, in salad dressings, margarines etc.) by inhibiting neutral fat deposition in humans. Processed oils produced from canola and soybean which contain increased proportions of diacylglycerol have been cited by the Kao Corporation of Japan (e.g. Econa Cooking Oil; Kao Corporation K1, 1-14-10 Nihonbashi-Kayabacho, Chuoku, Tokyo 103 Japan; e-mail: 210064@kastanet.kao.cojp) as a product making it difficult for blood neutral fat to increase after a meal, and for fat to cling to the body, thereby assisting individuals who are overweight or who suffer from high neutral fat levels. As a third example, silencing or reducing the activity of DGAT in a seed specific manner (as observed in mutant AS11; e.g. by over-expressing SEQ ID NO:23 or silencing expression of SEQ ID NO:1 or SEQ ID NO:3), and combining this trait with the capacity to produce polyhydroxyalkanoates (PHAs; e.g. polyhydroxybutyrate) in seeds (Poirier et al., 1992; 1995) will allow an increased flow of unesterified fatty acids towards β-oxidation (Poirier et al., 1999). By recycling or diverting the unesterified fatty acids into β oxidation, the resulting acetyl-CoA moieties will lead to a significant increase in polyhydroxyalkanoates (PHAs) or a change in PHA composition (Poirier et al., 1999). Transgenic plants producing PHAs in seeds have potential for utility as biodegradable thermoplastics. However, up to now, the levels of PHAs produced have been relatively small (Poirier et al, 1992; 1995). The utility of transgenically reducing the DGAT activity to significantly enhance PHA production (e.g. 10-fold increase) in PHA-producing seeds is now possible, due to the current DGAT invention.

Some of the manipulations and deliverables which are possible using the DGAT gene or a part thereof, include, but are not limited to, the following: seeds with increased or decreased oil content; seeds containing oils with an enhanced diacylglycerol content, seed oils with an altered acyl composition; plants producing larger or heavier seeds; plants exhibiting an enhanced or altered capacity to accumulate storage compounds in other storage organs (e.g. tubers, roots).

------.

The putative diacylglycerol binding site is overlined thus:

=====

The SnRK1 targeting site is overlined thus:

== with an asterisk (*) over the serine (S) residue as the targeted phosphorylation site.

Figure 5B:
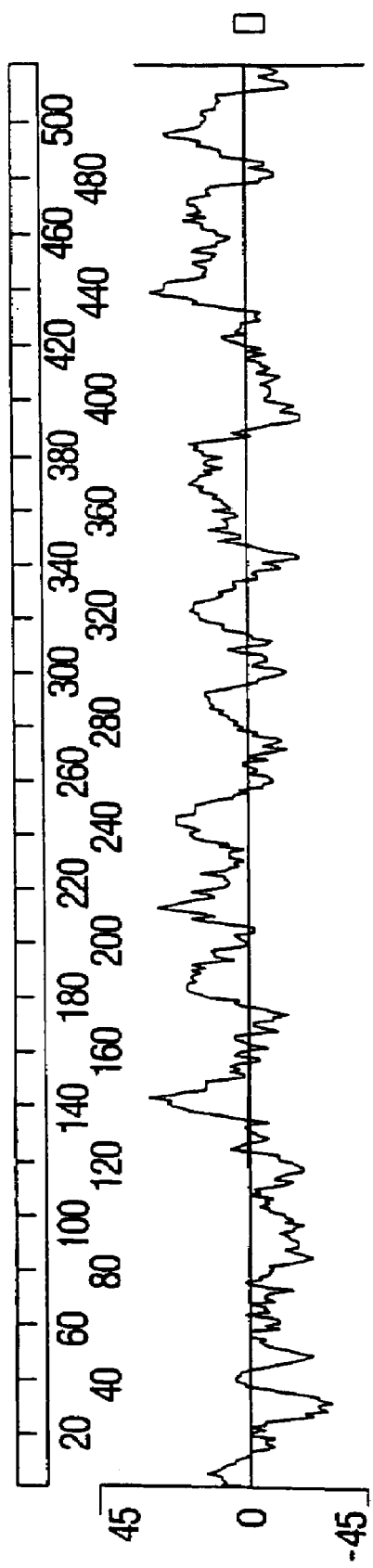
FIG. 5(*a*) shows the amino acid sequence alignment of the *Arabidopsis* DGAT (AtTAG1) (SEQ ID NO:2) with mammalian (mouse and putative human) DGATs. MDGAT, mouse DGAT (SEQ ID NO:4); GenBank/EMBL Accession No. AF078752 (Cases et al., 1998); HARGP1, human ARGP1 protein (SEQ ID NO:5); GenBank/EMBL Accession No. AF059202; Oelkers et al., 1998). Dots indicate gaps. Identical amino acid residues are highlighted in black. Conserved residues are shaded. The 27-amino acid repeat found in *Arabidopsis thaliana* mutant AS11 and generated by the insertion mutation (81 bp) found in SEQ ID NO:23 (SHAGLFNLCV-VVLIAVNSRLIIENLMK) is overlined thus.

FIG. 5(*b*) shows the Kyte-Doolittle hydropathy plot of the DGAT protein.

FIG. 6(*a*) shows the results of a Northern analysis of TAG1 gene expression in *Arabidopsis thaliana*. Total RNA was extracted from roots (RT), leaves (LF), flowers (FL), young seedlings (YS), developing siliques (SL), and germinating seeds (GS).

FIG. 6(*b*) shows the results of Southern blot analysis of the TAG1 gene in *Arabidopsis thaliana*. Genomic DNA was digested with restriction enzymes BglII (Lane 1), EcoRI (Lane 2), and HindIII (Lane 3). The TAG1 DNA probe was $^{32}$P labeled by random priming.

FIG. 7(*a*) is a diagrammatic representation of the TAG1 gene structure. The boxes indicate the 16 exons (solid boxes for coding regions, open box for untranslated regions), and the lines represent the 15 introns. A, B and C denote the positions of the primers used for PCR amplifications of the segments from wild type (WT) and AS11. The specific primers A, B and C are described in Experimental Procedures: Primer Strategy (found later in this specification).

FIG. 7(*b*) shows gel separation of the PCR products amplified from wild type (WT) and AS11. Lane 1, PCR product with primers A and B using WT genomic DNA as template. Lane 2, PCR product with primers A and B using AS11 genomic DNA as template. Lane 3, PCR product with primers C and B using WT genomic DNA as template. Lane 4, PCR product with primers C and B using AS11 genomic DNA as template. Lane 5, RT-PCR with primers A and B using RNA prepared from WT seedling RNA. Lane 6, RT-PCR with primers A and B using RNA prepared from AS11 seedling RNA.

Figure 8:
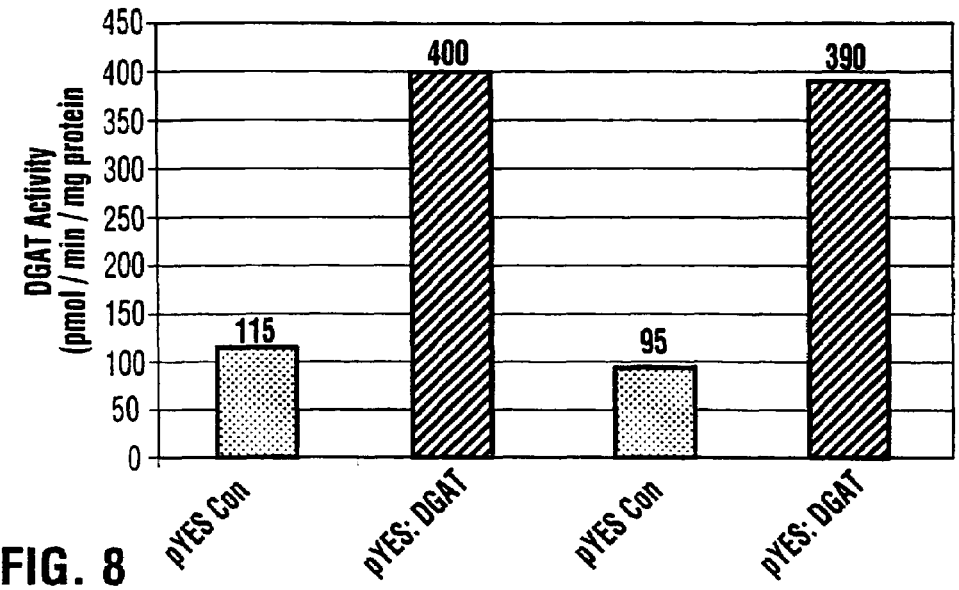

FIG. 8 is a graph showing microsomal DGAT activity in Yeast Strain YMN5 Transformed with empty plasmid (PYES Con) and with the *A. thaliana* DGAT cDNA (pYES:DGAT).

This illustrates the expression of the TAG1 cDNA in yeast. Host cultures of strain YMN5 were transformed with pYES2 plasmid only (pYES2; without TAG1 insert) or with pYES2 containing the TAG1 cDNA insert (pYES2:TAG1). Following induction in the presence of galactose, transformants were lysed and assayed for DGAT activity as described in the Experimental Procedures. The results of two separate DGAT activity experiments are shown.

Figure 9:
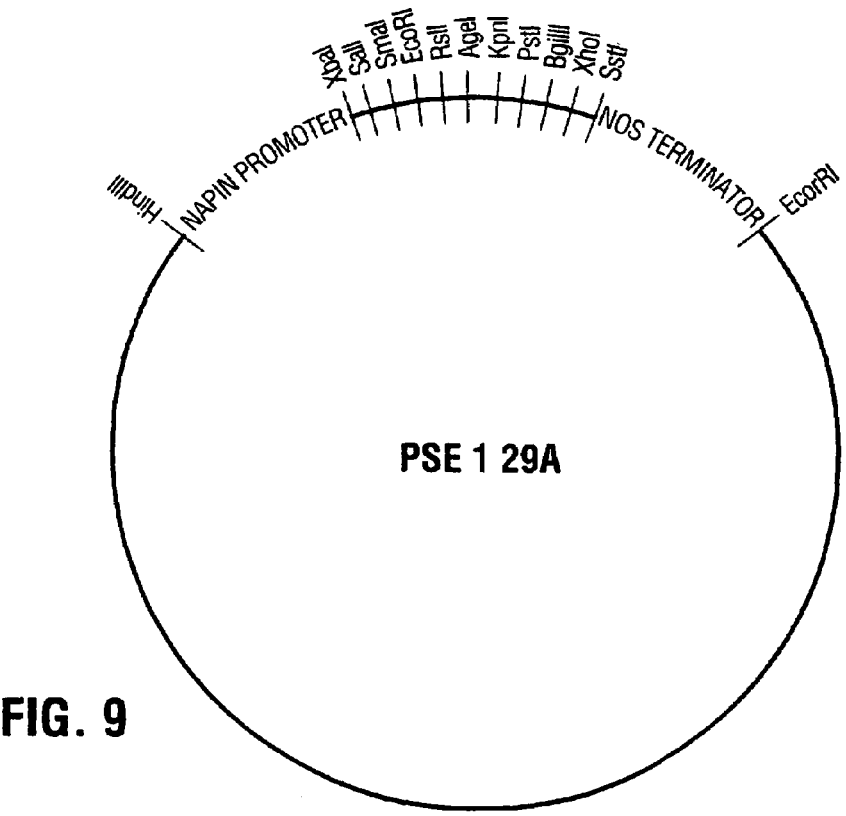

FIG. 9 is a map of plasmid pSE129A which may be used as a vector. The vector contains the following salient features for plant transformation in the current invention: the seed-specific napin promoter and NOS terminator between which is a multiple cloning site.

Figure 10:
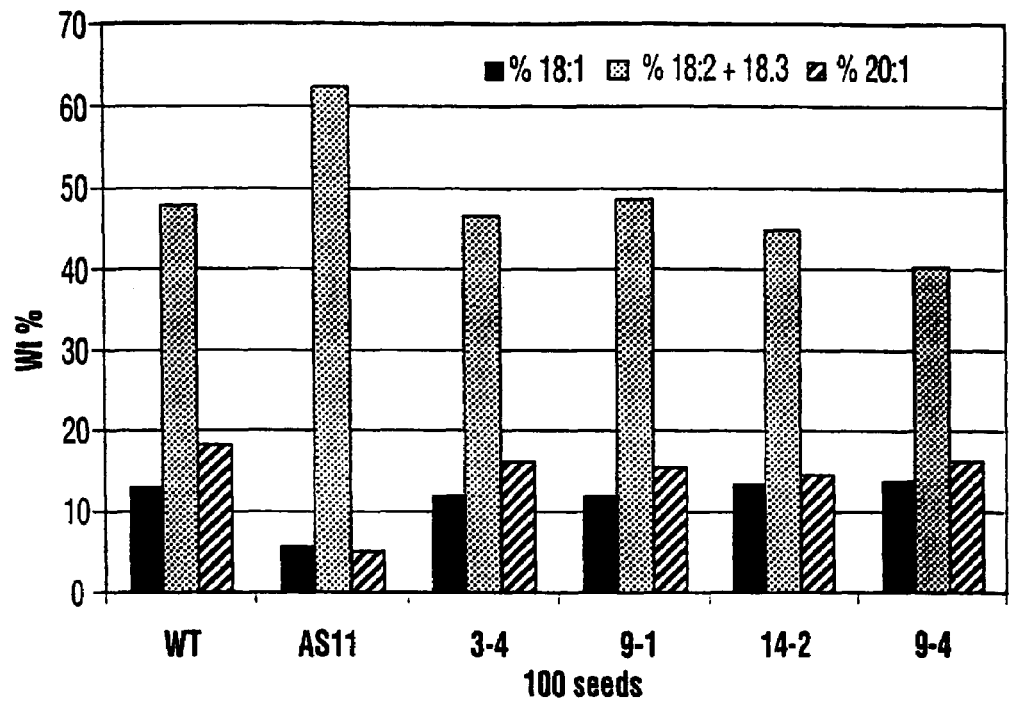

FIG. 10 is a graph showing the complementation of the AS11 DGAT mutation with the wild-type cDNA. Transformation of *Arabidopsis thaliana* mutant line AS11 with the DGAT cDNA [SEQ ID NO:1] under the control of a napin promoter, leads to a restoration of the wild-type (WT) fatty acid composition in the seed oil of the transformant lines 3-4, 9-1, 14-2 and 9-4. Fatty acid composition (wt %) was determined on the seed oil extracted from 100-seed samples from *A. thaliana* non-transformed controls (WT), mutant line AS 11, and T$_2$ seeds of napin:DGAT transgenic lines.

Figure 11:
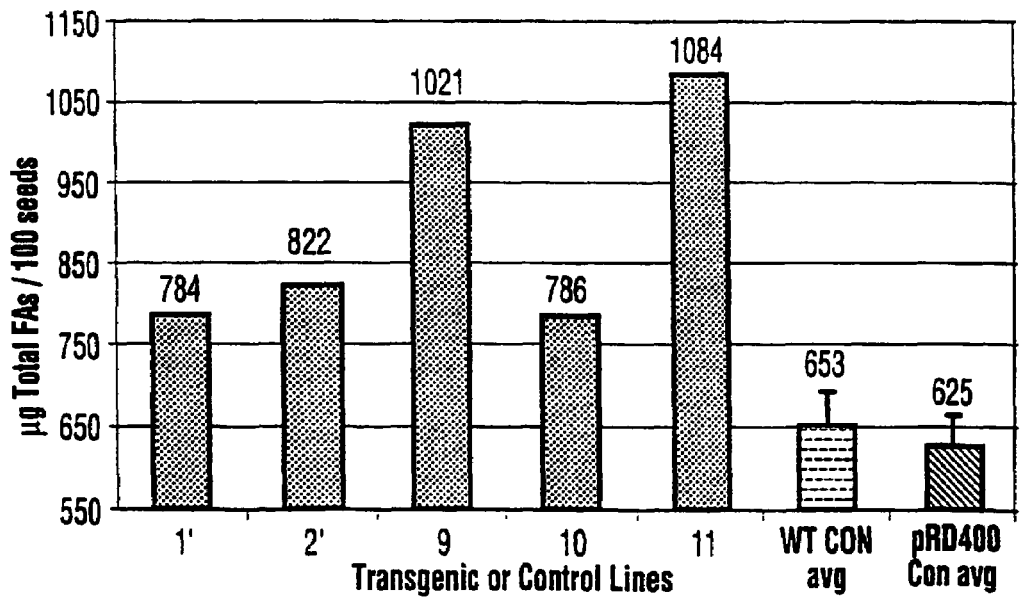

FIG. 11 is a graph showing the seed oil content of non-transformed WT control, and pRD400 control (empty plasmid) and napin:DGAT T$_2$ transgenic *Arabidopsis thaliana* seed lines. More particularly, the graph shows the transformation of wild type (WT) *Arabidopsis thaliana* with the DGAT cDNA (SEQ ID NO:1) under the control of a napin promoter, leads to a higher seed oil content in the DGAT transgenic lines. Oil content is expressed as µg total fatty acids (FAs) per 100 seeds from *A. thaliana* non-transformed controls (WT Con), and T$_2$ seeds of pRD400 control (empty plasmid) transgenic, and napin:DGAT transgenic lines 1', 2', 9, 10 and 11. Standard error bars for the control lines are indicated; n=10.

Figure 12:
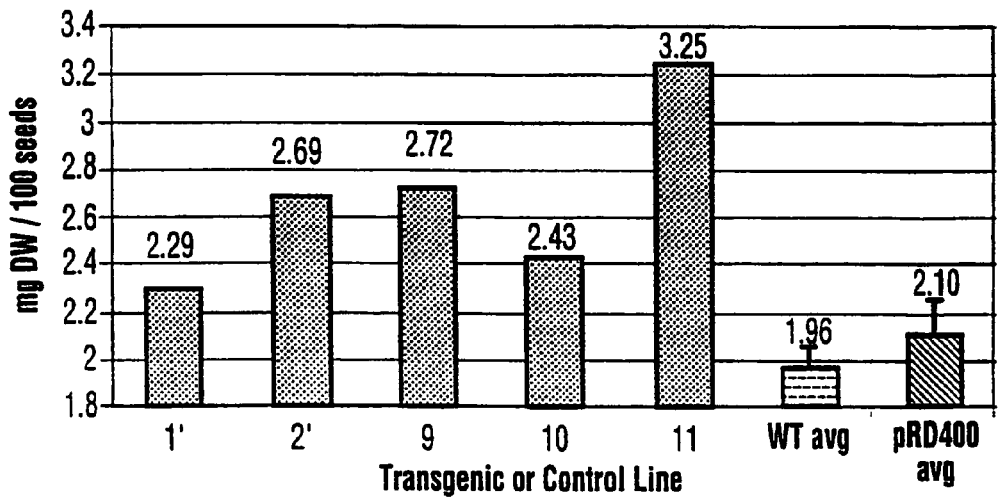

FIG. 12 is a graph showing the average 100-seed weight of non-transformed WT control, and pRD400 control (empty plasmid) and napin:DGAT T$_2$ transgenic *Arabidopsis thaliana* seed lines. More specifically, the graph shows the over-expression of the DGAT cDNA under the control of a napin promoter, in wild-type (WT) *Arabidopsis thaliana* leads to a higher average seed weight. The average weight of 100-seed samples from *A. thaliana* non-transformed controls (WT Con), and T$_2$ seeds of pRD400 control (empty plasmid) transgenic, and napin:DGAT transgenic lines 1', 2', 9, 10 and 11 are reported as mg dry weight (DW).

Figure 13:
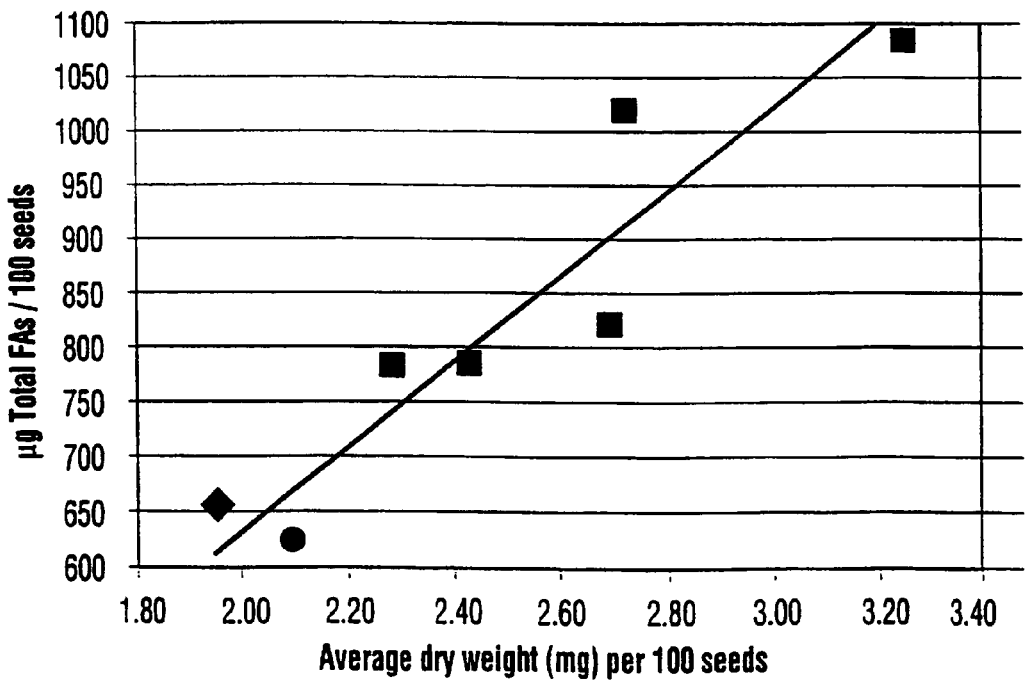

FIG. 13 is a graph showing the positive correlation between oil content (expressed as µg Total fatty acids (FAs) per 100 seeds) and average seed weight (expressed as average mg DW per 100-seed samples) from *A. thaliana* non-transformed controls (WT Con ♦), and T2 seeds of pRD400 control (empty plasmid) transgenic (0 and napin:DGAT transgenic lines 1', 2', 9, 10 and 11(■) are reported as mg dry weight (DW).

BEST MODE OF THE INVENTION

Figure 1:
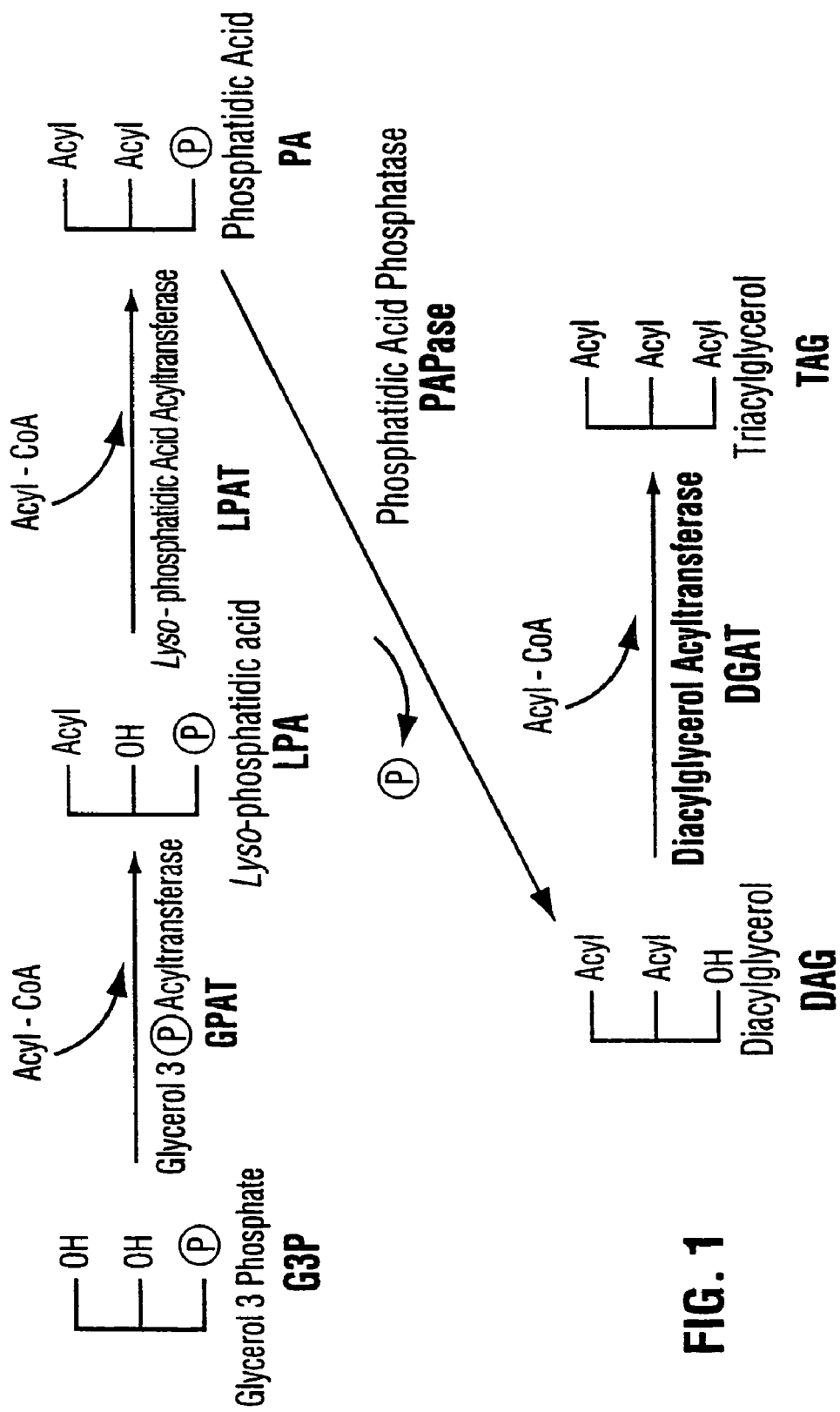
FIG. 1 is a diagram illustrating the Kennedy pathway for the bioassembly of triacylglycerols in plants, and shows the critical role played by DGAT as the final step of the Kennedy pathway.

FIG. 1 is a diagram illustrating the Kennedy pathway for the biosynthesis of TAGs in plants. Of the various illustrated enzymes, DGAT is the only enzyme in the Kennedy pathway that is exclusively committed to TAG biosynthesis, and its key role is apparent from the scheme of FIG. 1. sn-1,2-DAG, generated as a result of either the catalytic action of PA phosphatase (EC 3.1.3.4) or CPTase (EC 2.7.8.2), can be used in the biosynthesis of TAG.

For this reason, the inventors of the present invention decided to investigate DGAT to see if the corresponding gene in plants could be sequenced and cloned and used to modify the seed oil content and fatty acid composition of plants in a way that could be commercially useful.

The acyl-CoA dependent acylation of sn-1,2-DAG is catalyzed by DGAT (Stymne and Stobart, 1987). In developing and germinating seeds of oilseed plants, TAG accumulation and DGAT activity have been shown to associate with the endoplasmic reticulum (ER; high speed microsomal fraction) (Stobart et al., 1986; Cao and Huang, 1986; Stymne and Stobart, 1987; Frentzen, 1993; Settlage et al, 1995; Lacey and Hills, 1996). The biochemical properties of microsomal DGAT have been examined in a number of plant systems (Frentzen, 1993) including developing seeds (Bernerth and Frentzen, 1990; Vogel and Browse, 1996; Cao and Huang, 1987) and embryo cultures (Taylor et al., 1991; Weselake et al., 1991; Taylor et al., 1992; Little et al., 1994) of *B. napus L*. In general, studies with developing seeds indicate that DGAT activity increased rapidly during the active phase of oil accumulation and then decreases markedly as seed lipid content reaches a plateau (Tzen et al., 1993; Weselake et al., 1993).

A number of studies with both mammalian (Mayorek et al., 1989; Tijburg et al., 1989) and plant (Ichihara et al., 1988; Perry and Harwood, 1993 a and 1993 b; Settlage et al. 1995) systems have suggested that DGAT may catalyze a rate-limiting reaction in TAG bioassembly. However, this hypothesis has not been rigorously tested, and has not been reduced to practice by transgenic expression of any DGAT gene in plant or animal systems, until now. Developing seeds of *B. napus L.*, cv Shiralee, have been shown to produce significant levels of DAG during the active phase of oil accumulation suggesting that DGAT catalyzed reaction may regulate the flow of carbon into TAG (Perry and Harwood, 1993 a and 1993 b). In addition, an ethyl methanesulfonate-induced (EMS-induced) mutant of *A. thaliana*, designated AS11, has been shown to have a reduced DGAT activity that correlated with both an increased DAG pool and decreased accumulation of TAG (Katavic et al. 1995). Given its possible rate-limiting role in TAG bioassembly, the inventors of the present invention have identified DGAT as a potential target in the genetic modification of plant lipid biosynthesis.

Figure 2:
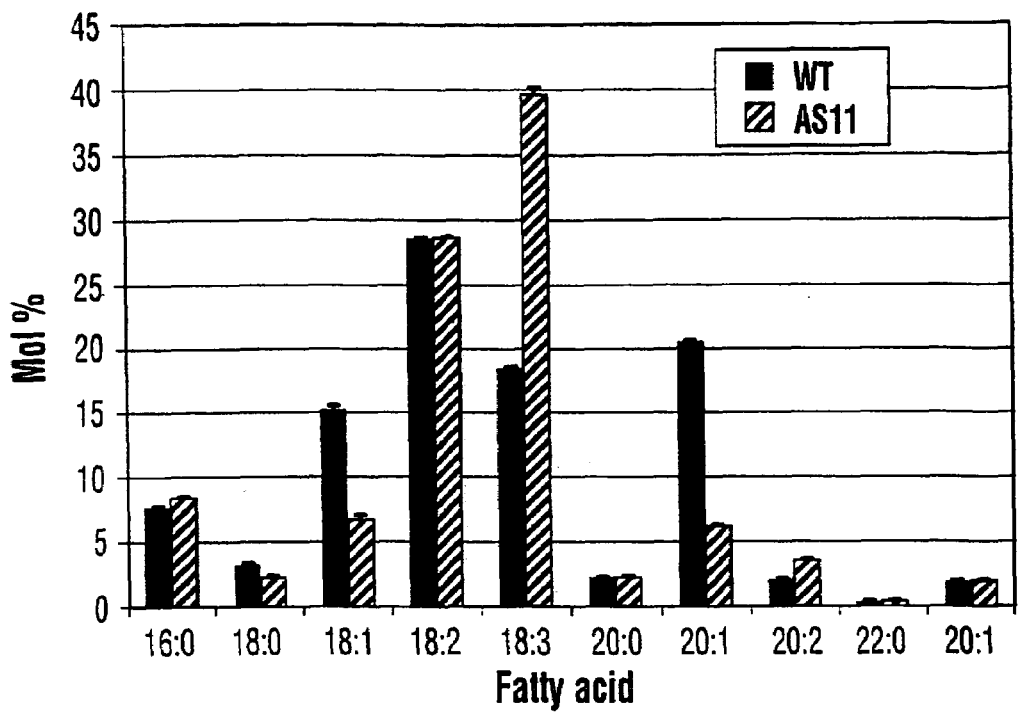
FIG. 2 is a graph showing the comparison of the fatty acid composition of seed oil from wild-type (WT) and DGAT mutant AS 11 lines of *Arabidopsis thaliana*. Proportions of fatty acids are reported as Mol % of the total fatty acid composition of the seed oil from each line. Error bars are ±SE (n=10 plants of each line sampled, with 50 seeds per sample per analysis).
Figure 3:
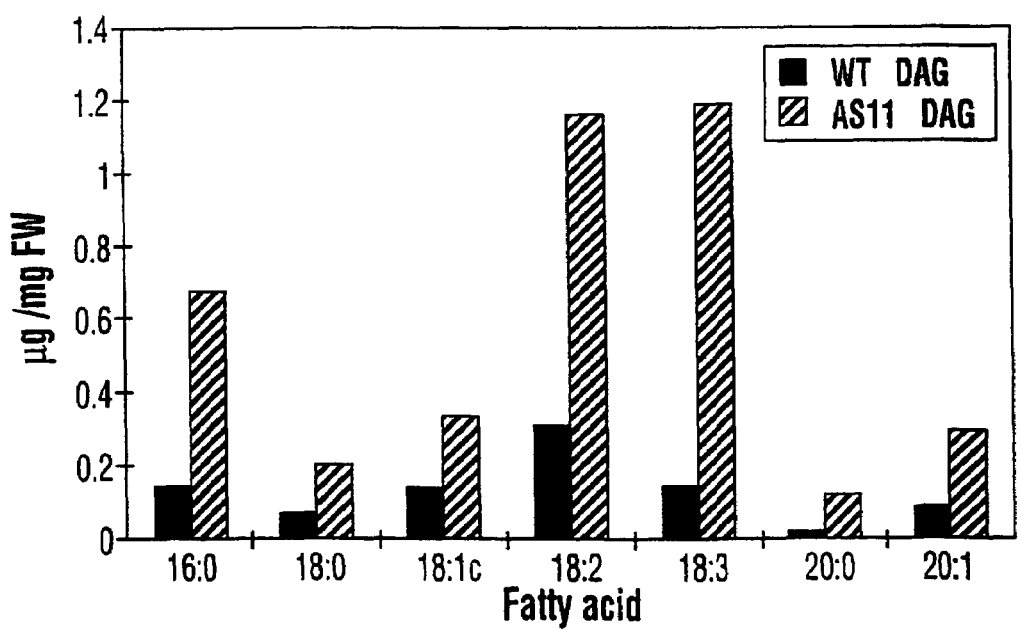
FIG. 3 is a graph showing a comparison of the DAG content in developing seed of wild-type (WT) and DGAT mutant AS11 lines of *Arabidopsis thaliana*. More specifically, it is a comparison of the fatty acid content of DAG pool in wild-type green developing seeds compared to that of the AS11 mutant.
Figure 4:
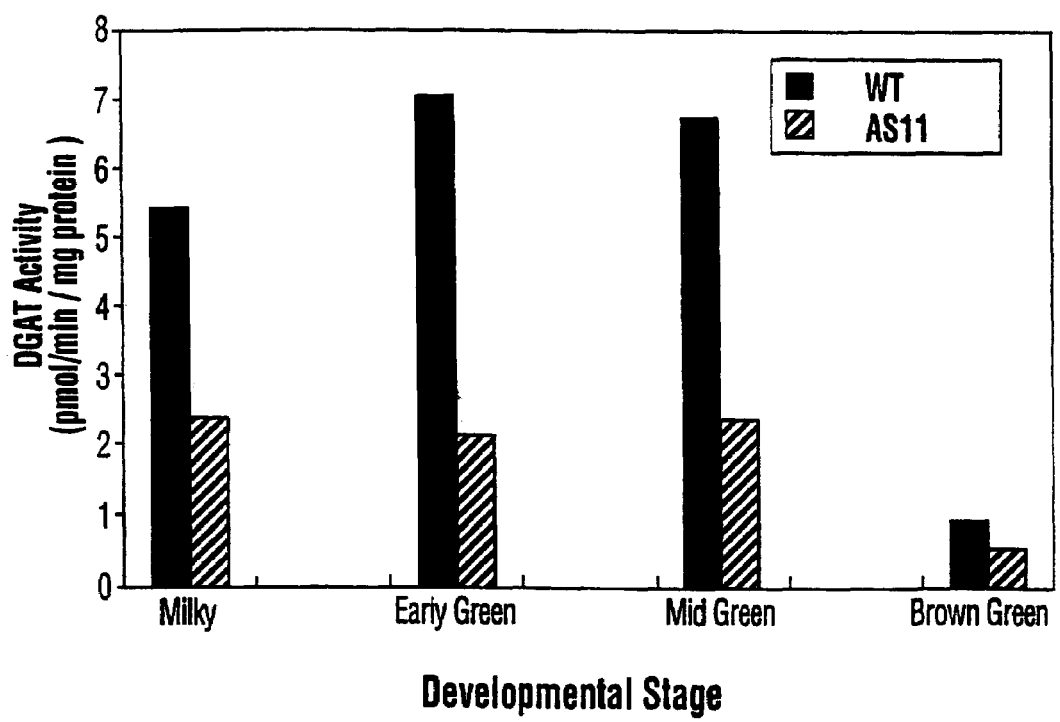
FIG. 4 is a graph showing a comparison of the DGAT activity (pmol/min/mg protein) in developing seeds at the milky, early green, mid-green and brown-green stages of embryo development in wild-type (WT) and DGAT mutant AS 11 lines of *Arabidopsis thaliana*. Developing seeds at each stage were selected and DGAT enzyme analyses conducted as described previously by Katavic et al., 1995).

Previously, the partial characterization of an EMS-induced *Arabidopsis thaliana* mutant, AS11, with altered fatty acid composition was reported (Katavic et al., 1995). In comparison to wild type plant seeds, AS11 seeds have reduced levels of the very long chain fatty acid eicosanoic acid (20:1) and reduced oleic acid (18:1) and accumulate α-linolenic acid (18:3) as the major fatty acid in triacylglycerols (FIG. 2). The AS11 mutant has a consistently lower ratio of TAG/DAG in developing seeds, and it accumulates an elevated amount of seed DAG (FIG. 3), the substrate of the diacylglycerol acyltransferase. Through a series of biochemical analyses, it was shown that AS11 had reduced diacylglycerol acyltransferase activities throughout seed development (FIG. 4). AS11 also had a reduced (by 25-30%) oil content phenotype, providing some evidence that DGAT may be controlling flux into TAG biosynthesis, as shown in Table 1 below. The AS11 did not have a wrinkled-seed phenotype as described in other low-seed-oil mutants (Focks and Benning, 1998).

TABLE 1

Comparison of AS11 [Katavic et al., (1995) and wild-type
*A. thaliana* seeds with respect to lipid profiles at
mid-development, and the relative TAG, DAG and sterol
ester contents in AS11 and WT seeds at maturity.

| Seed Type | TAG/DAG ratio at mid-development[a] | TAG/DAG ratio at maturity[a] | Relative TAG content at maturity[b] c(nmol/mg DW) | Sterol Esters at maturity (% of Total Lipid Extract)[d] |
|---|---|---|---|---|
| WT | 17 | 90 | 1.00[b] [c](255) | 0.8 |
| AS11 | 5 | 20 | 0.6[b] [c](174) | 1.15 |

[a]Embryos staged and lipids measured as described in Katavic et al., (1995);
[b]Relative TAG content of 200-seed samples of AS11 and WT were measured by MASS-1H-NMR according to the method of Rutar (1989). The integration response for resonances attributable to liquid-like oil were summed and the value for AS11 seed is reported relative to the response for the WT control seed sample (the latter set at a value of 1.00);
[c]TAG content (nmoles/mg DW) measured by transmethylation of a TLC-purified TAG fraction, followed by GC analysis of fatty acid methyl esters;
[d]A total lipid extract was prepared as described by Taylor et al., (1991; 1992), and sterol esters isolated and characterized as described in the Experimental Procedures.

Genetic analysis indicated that the fatty acid phenotype is caused by a semidominant mutation in a nuclear gene, designated TAG 1. The mutation was mapped to chromosome II, and was estimated to lie in the region approximately 17.5±3 cM from the sti locus and 8±2 cM from the cp2 locus.

Because a DGAT gene has not heretofore been cloned from any plant, until now, it has not been possible to address the possibility of genetic modifications to alter carbon flux, increase fatty acid synthesis, oil content, oil acyl composition, or seed size, by modulating plant DGAT activity.

However, there are many examples of successful modifications to plant metabolism that have been achieved by genetic engineering to transfer new genes or to alter the expression of existing genes, in plants. It is now routinely possible to introduce genes into many plant species of agronomic significance to improve crop performance (e.g. seed oil or tuber starch content/composition; meal improvement; herbicide, disease or insect resistance; heavy metal tolerance etc.) (MacKenzie and Jain, 1997; Budziszewski et al., 1996; Somerville, 1993; Kishore and Somerville, 1993).

For example, increases in the proportions of some strategic fatty acids and in the quantities of seed oil have been achieved by the introduction of various fatty acid biosynthesis and acyltransferase genes in oilseed crops. These include the following demonstrations: Expression of an anti-sense construct to the stearoyl-ACP Δ9 desaturase in Brassicaceae led to an increase in the stearic acid content (Knutzon et al., 1992). Expression of a medium chain fatty acyl-ACP thioesterase from California Bay, in Brassicaceae was demonstrated to increase the lauric acid (12:0) content (Voelker et al., 1992; 1996). Expression of a Jojoba β keto-acyl-CoA synthase in low erucic acid Brassicaceae led to an increase the level of erucic acid (22:1); the effect following expression in high erucic acid cultivars was negligible (Lassner et al., 1996). Increased proportions of oleic acid in *Brassica napus* and in soybean have been achieved by silencing the microsomal FAD2 (Δ12) desaturase (Hitz et al., 1995; Kinney, 1995; 1997). Transformation of *Arabidopsis thaliana* and rapeseed (*B. napus*) with a yeast sn-2 acyltransferase resulted in seed oils with increased proportions of 22:1 and other very long-chain fatty acids and significant increases in seed oil content (Zou et al., 1997).

Starch deposition has also been altered by genetic engineering. By expression of a mutant *E. coli* glgC16 gene encoding an ADP glucose pyrophosphorylase in potato tubers, an increase in starch accumulation was achieved (Stark et al., 1992).

The inventors therefore considered the DGAT gene to hold great promise for the desired modification of TAGs in plants.

The best modes for carrying out the invention will be apparent from the following description of the results of tests and experiments that have been carried out by the inventors.

The inventors chose to use the well-accepted model plant system *Arabidopsis thaliana* for the cloning of DGAT, as a host system for genetic engineering to alter DGAT expression, and to study the effects of altering DGAT expression on seed triacylglycerol bioassembly. This is because, over the past several years, *Arabidopsis thaliana*, a typical flowering plant, has gained increasing popularity as a model system for the study of plant biology. As a result of the ease with which this plant lends itself to work in both classical and molecular genetics, *Arabidopsis* has come to be widely used as a model organism in plant molecular genetics, development, physiology and biochemistry (Meyerowitz and Chang, 1985; Meyerowitz, 1987; Goodman et al., 1995). This model dicotyledonous plant is also closely related to *Brassica* crop species and it is increasingly apparent that information concerning the genetic control of basic biological processes in *Arabidopsis* will be transferable to other species (Lagercrantz et al., 1996).

Indeed, there are numerous examples wherein studies of the molecular biology and biochemistry of a particular metabolic pathway or developmental process and the possibility of genetically engineering a plant to bring about changes to said metabolic pathway or process, has first been tested in the model plant *Arabidopsis*, and then shown to yield similar phenotypes in other plants, particularly crop plants.

For example, the extra-plastidial membrane associated oleate (18:1) Δ12 (ω-6) desaturase gene, FAD2, was originally studied and eventually cloned from *Arabidopsis thaliana*, by identifying the lesion found in an *A. thaliana* mutant defective in desaturating oleate to produce linoleate (18:2) on the phosphatidylcholine backbone. This resulted in a high oleic acid phenotype in the *A. thaliana* seed oil (Okuley et al., 1994). Genetic engineering of both soybean (*Glycine max.*) and canola *B. napus* to silence the indigenous FAD2 gene(s) in a seed-specific manner by anti-sense or co-suppression approaches, resulted in similar high oleic acid seed oil phenotypes (Kinney, 1995; 1997).

Transgenic expression of a yeast sn-2 acyltransferase (SLC1-1) gene to achieve enhanced seed oil and very long-chain fatty acid content was first performed in *Arabidopsis* and later shown to yield similar phenotypes in transgenic rapeseed (*B. napus*) experiments (Zou et al., 1997). *Arabidopsis thaliana* has repeatedly shown itself to be a useful model system for metabolic engineering of metabolic pathways (e.g. lipid biosynthesis, photosynthesis) or processes (organogenesis, reproductive development etc.) common to all higher plants.

In the area of secondary metabolism/signal transduction, an anthocyanin pathway-specific transcriptional activator from the monocot maize designated as R (the myc transcription factor involved in activation of biosynthetic genes for anthocyanin production in the aleurone cells of maize kernels), was expressed in the dicot *Arabidopsis*, causing augmented anthocyanin pigmentation in the inflorescences. Subsequent expression in another dicot, tobacco (*Nicotiana tabacum*), resulted in similar floral pigmentation changes (Lloyd et al., 1992). These experiments demonstrate that whole pathways common to all flowering plants can be coordinately controlled through the introduction of transcriptional regulators, and that the mechanisms are common to diverse plant species.

In the context of the current invention, all plant seeds accumulate some triacylglycerol (oil) and this ubiquitous process is affected, at least in part, by the activity of a microsomal DGAT, as explained previously. Thus, many of the effects observed following genetic engineering to modulate DGAT expression in *Arabidopsis* can be expected and predicted to result in similar phenotypes when carried out in all other plants. For example, after the present invention was made, information has become available that supports the findings of the present inventors by showing that *B. napus* has a highly homologous DGAT gene (Nikiforuk et al., 1999), and thus *B. napus* is a clear target for similar genetic modifications as those shown for *A. thaliana*.

There are a number of ways by which genes and gene constructs can be introduced into plants, and a combination of plant transformation and tissue culture techniques have been successfully integrated into effective strategies for creating transgenic crop plants. These methods, which can be used in the present invention, have been extensively reviewed elsewhere (Potrykus, 1991; Vasil, 1994; Walden and Wingender, 1995; Songstad et al., 1995), and are well known to persons skilled in the art. For example, one skilled in the art will certainly be aware that, in addition to *Agrobacterium*-mediated transformation of *Arabidopsis* by vacuum infiltration (Bechtold et al., 1993) or wound inoculation (Katavic et al., 1994), it is equally possible to transform other plant and crop species, using *Agrobacterium* Ti-plasmid-mediated transformation (e.g. hypocotyl (DeBlock et al., 1989) or cotyledonary petiole (Moloney et al, 1989) wound infection), particle bombardment/biolistic methods (Sanford et al., 1987; Nehra et al., 1994; Becker et al., 1994) or polyethylene glycol-assisted protoplast transformation (Rhodes et al., 1988; Shimamoto et al., 1989) methods.

As will also be apparent to persons skilled in the art, and as extensively reviewed elsewhere (Meyer, 1995; Datla et al., 1997), it is possible to utilize plant promoters to direct any intended up- or down-regulation of transgene expression using constitutive promoters (e.g. those based on CaMV35S), or by using promoters which can target gene expression to particular cells, tissues (e.g. napin promoter for expression of transgenes in developing seed cotyledons), organs (e.g. roots), to a particular developmental stage, or in response to a particular external stimulus (e.g. heat shock).

Particularly preferred plants for modification according to the present invention include *Arabidopsis thaliana*, borage (*Borago* spp.), Canola, castor (*Ricinus communis*), cocoa bean (*Theobroma cacao*), corn (*Zea mays*), cotton (*Gossypium* spp), *Crambe* spp., *Cuphea* spp., flax (*Linum* spp.), *Lesquerella* and *Limnanthes* spp., Linola, nasturtium (*Tropaeolum* spp.), *Oenothera* spp., olive (*Olea* spp.), palm (*Elaeis* spp.), peanut (*Arachis* spp.), rapeseed, safflower (*Carthamus* spp.), soybean (*Glycine* and *Soja* spp.), sunflower (*Helianthus* spp.), tobacco (*Nicotiana* spp.), *Vernonia* spp., wheat (*Triticum* spp.), barley (*Hordeum* spp.), rice (*Oryza* spp.), oat (*Avena* spp.) sorghum (*Sorghum* spp.), rye (*Secale* spp.) or other members of the Gramineae.

The present invention is particularly useful when used to modify the yield or composition of oilseed produced from oilseed crops. Oilseed crops are plant species that are capable of generating edible or industrially useful oils in commercially significant yields, and include many of the plant species listed above. Such oilseed crops are well known to persons skilled in the art.

EXAMPLES

Example 1

Isolation of the TAG 1 (DGAT) cDNA from *Arabidopsis thaliana*

Since one of the most likely defects in AS11 mutant is at the DGAT itself (Table 1; FIG. 4), the inventors attempted cloning strategies based on sequence information of enzymes that share common substrates with DGAT. One of the candidate enzymes that would serve this purpose is the acyl-CoA: cholesterol acyltransferase (ACAT, EC 2.3.1.26) (Chang et al., 1997). Like DGAT, ACAT is an ER protein functioning as an O-acyltransferase by using acyl-CoA as the fatty acyl donor for the esterification of free cholesterol to generate sterol esters. Through a BLAST database search, the inventors identified an *Arabidopsis thaliana* expressed sequence tag (EST) (accession no. AA042298; SEQ ID NO:6) with a deduced amino acid sequence showing 41% identity to that of the yeast acyl-CoA: cholesterol acyltransferase (Yang et al., 1996, Yu et al., 1996), within the short sequence (104 amino acids) that was available for the EST.

The corresponding cDNA (E6B2T7) clone was obtained from the *Arabidopsis* Biological Resource Center, Columbus, Ohio. Upon complete sequencing, the 878 bp E6B2T7 clone was found to be a partial cDNA. However, the ORF prediction from this partial cDNA confirmed the initial EST search results in that the encoded product is structurally similar to ACAT, especially in the regions at the C-terminus. The inventors were confident that the cDNA contained the 3' untranslated region through an ORF search, although the polyA tail was missing.

The inventors further used the partial cDNA sequence to search against *Arabidopsis thaliana* genomic sequence information. An *Arabidopsis* 'IGF' BAC clone 'F27F23' (accession no. AC003058) was identified to include a region that matched the cDNA, and therefore it was concluded that this was the region encompassing the corresponding gene. Moreover, this BAC clone 'F27F23', is contained in the YAC clone, CIC06EO8, which, according to the published map position (http://weeds.mgh.harvard.edu/goodman/c2_b.html), represents a region between centimorgan 35.9 and centimorgan 38.7 on chromosome II; this position is similar to the estimated location for TAG1, and the lesion identified by the mutation in AS11 (Katavic et al., 1995). In view of our previous results on the characterization of the AS 11 mutant, the map position of this gene strongly suggested that it may encode a DGAT.

To clone a full-length cDNA, a series of oligonucleotide primers were designed, based on the genomic sequences located at different positions 5' upstream of the region covering the partial cDNA. We used these primers in combination with a primer located at the 3' UTR of the partial cDNA (E6B2T7) to perform PCR reactions with cDNA phagemid prepared from an *Arabidopsis thaliana* (ecotype Columbia) silique-specific cDNA library (Giraudat et al., 1992) as a template. The longest cDNA amplified was 1904 bp, which we subsequently designated as TAG1, and deposited into the Genbank under accession AJ238008 (SEQ ID NO:1). We believe this cDNA represents a full-length clone because its size is in agreement with that of the transcript detected in the northern blot (see FIG. 6a). The longest open reading frame is flanked by a 134-nucleotide 5' untranslated region and a 203-nucleotide 3' untranslated region. There is an in-frame stop codon (TGA at position nt43) which is followed by an in-frame ATG at position nt-139. It is thus inferred that the ATG at position nt-139 is the initiation codon.

Example 2

The primary structure of TAG1 predicts a DGAT-related enzyme

The predicted open reading frame of the TAG1 cDNA encodes for a polypeptide of 520 amino acids with a calculated molecular weight of 58993 Daltons. With the BLAST search program (Altschul et al. 1990), it was found that the recently reported mouse diacylglycerol acyltransferase (accession no. AF078752) (Cases et al., 1998) is a protein which showed the highest sequence similarity to the deduced amino acid sequence of TAG1 (FIG. 5a). TAG1 was also similar to a human acyl CoA: cholesterol acyltransferase-related enzyme (accession no. AF059202). The human acyl CoA: cholesterol acyltransferase-related enzyme, also known as ARGP1, is most likely to be a DGAT with no significant ACAT activity, although the true nature of the enzyme awaits further confirmation (Oelkers et al., 1998). The similarity between TAG1 and the mammalian DGAT extends over a region of more than 400 amino acids with a sequence identity of about 41%. A putative diacylglycerol/phorbol ester-binding motif, H-K-W-X-X-R-H-X-Y-X-P (SEQ ID NO:26), a signature sequence observed to be unique to DGAT while absent in the ACATs (Oelkers et al., 1998), is located at amino acids 414-424 (SEQ ID NO:7); FIG. 5a). This diacylglycerol binding motif is also found in the subsequently published B. napus DGAT sequences (Nikyiforuk et al., 1999; GenBank/EMBL Accession Nos. AF155224, SEQ ID NO:8; AF164434, SEQ ID NO:9). Among other cloned acyltransferases (e.g. GPATs, LPATs, dihydroxyacetone phosphate acyltransferases) it has been reported that there is an invariant proline in a highly hydrophobic block IV that may participate in acyl-CoA binding (Lewin et al., 1999). In the TAG1 sequence, the hydrophobic block from residues 221-229 containing an invariant proline at residue 224, might constitute such a motif.

TAG1 showed some sequence similarity to other acyl CoA: cholesterol acyltransferases from a number of species (Chang et al., 1997). However, the similarity is largely confined to the C-terminus and is lower (around 30%) than is the similarity of TAG1 to the mammalian DGAT.

The TAG1 protein has multiple hydrophobic domains (FIG. 5b) and an analysis by the PC Gene program predicted that the protein has 5 possible transmembrane segments (amino acids 178-195, 233-253, 363-388, 433-476, 486-507). In the mammalian DGAT, a putative tyrosine phosphorylation motif was observed (Cases et al., 1998), but no apparent tyrosine phosphorylation site could be found in TAG 1. However, a visual examination revealed a consensus sequence (X-L$^{200}$-X-K$^{202}$-X-X-S$^{205}$-X-X-X-V$^{209}$, SEQ ID NO:10) identified as a targeting motif typical of members of the SNRK1 protein kinase family, with serine residue 205 being the residue for phosphorylation. The SNRK1 (SNF1-related protein kinase-1) proteins are a class of Ser/Thr protein kinases that have been increasingly implicated in the global regulation of carbon metabolism in plants (Halford and Hardie, 1998). This consensus SnRK1 targeting motif is also found in the subsequently published B. napus DGAT sequences (Nikyiforuk et al, 1999; GenBank/EMBL Accession Nos. AF155224; AF164434). Interestingly, similar SnRK1 targeting motifs could also be identified in the lysophosphatidic acid acyltransferases (LPATs) from coconut (Knutzon et al., 1995) and meadowfoam (Lassner et al., 1995), respectively.

Example 3

The TAG1 gene is Ubiquitously Expressed in Arabidopsis

Figure 6A:
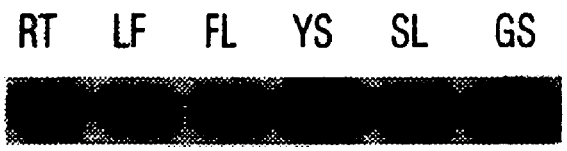

Northern blot analyses were performed to investigate the expression profile of the TAG1 gene. Total RNA was extracted from different tissues, including roots, leaves, flowers, developing siliques, young seedlings and germinating seeds. The highest steady-state level accumulation of TAG1 transcript was in RNA isolated from germinating seeds and young seedlings (FIG. 6a). TAG1 transcripts were also detected in root, leaf and flower tissues, albeit at lower levels. Surprisingly, the TAG1 gene is expressed in developing siliques at a level that is comparable to that of other vegetative tissues, but lower than that of germinating seeds and young seedlings. This expression profile in general is not inconsistent with the notion that DGAT is present in all plant tissues capable of TAG biosynthesis (Kwanyuan and Wilson, 1986). It has been shown in a number of plant species, including soybean and safflower, that germinating seeds actively synthesize TAGs (Ichihara and Noda, 1981; Kwanyuan and Wilson, 1986; Wilson and Kwanyuan, 1986). The relatively high level of expression in roots is also consistent with the fact that root plastids are capable of synthesizing large amounts of triacylglycerol (Sparace et al., 1992).

Figure 6B:
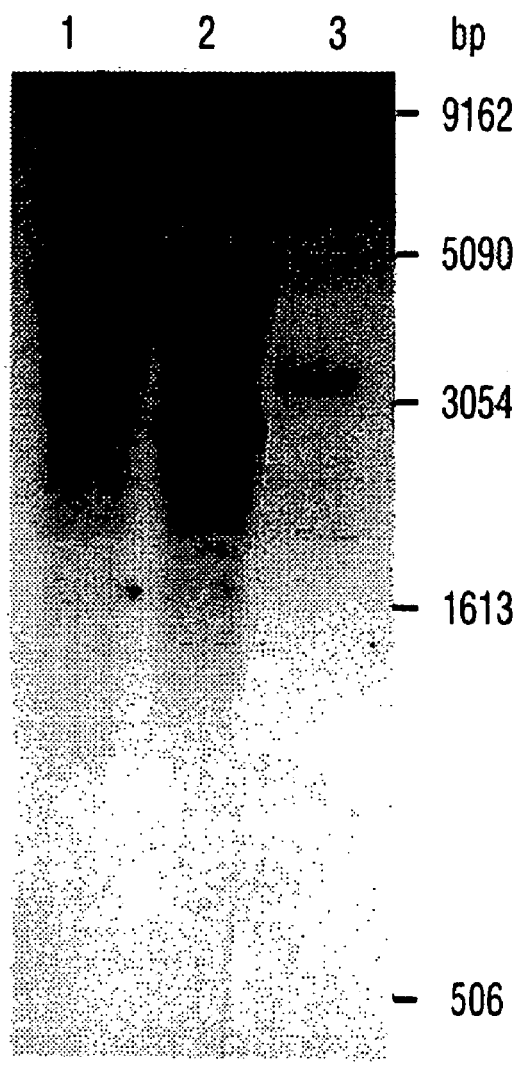

Southern blot hybridization (Southern, 1975) was performed with genomic DNA digested with several restriction enzymes including BglII, EcoRI and HindIII. The TAG1 gene has no internal BglII and HindIII site, while one internal EcoRI site exists. Our Southern analysis suggested that TAG1 most likely represents a single copy gene in the Arabidopsis genome (FIG. 6b).

Example 4

An Insertion Mutation is Found in the TAG1 Gene in mutantASli

Figure 7A:
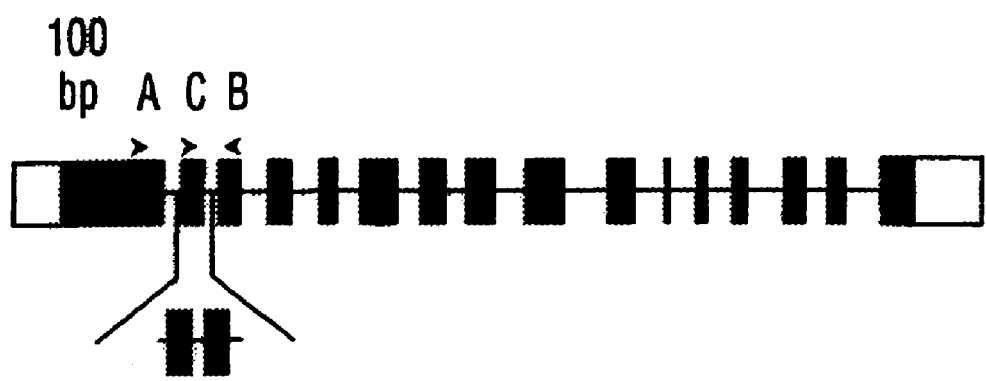

Alignment of the genomic sequence (accession no. AC003058; SEQ ID NO:3) with that of the TAG1 cDNA (SEQ ID NO:1) revealed that the TAG1 gene contains 16 exons and 15 introns, spanning a region of about 3.4 kb (FIG. 7a). DNA containing the TAG1 allele from AS11 was PCR-amplified and completely sequenced. The AS11 TAG1 allele has a 147-bp insertion located at the central region of intron 2. The insertion is a duplication of a segment that is composed of 12 bp from the 3' end of intron 1, the entire sequence of exon 2 (81 bp) and 54 bp from the 5' end of intron 2 (FIG. 7a).

Figure 7B:
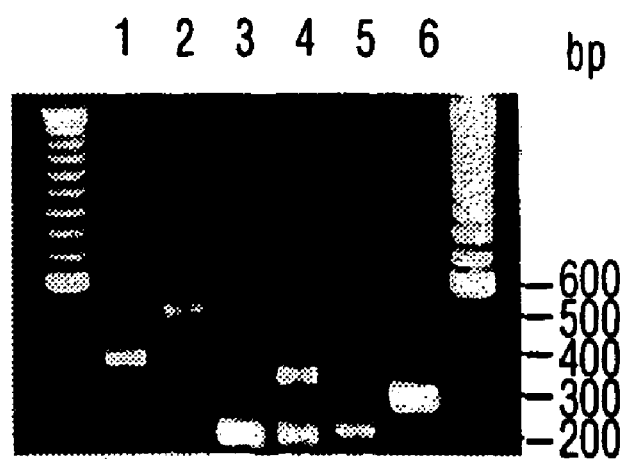

In order to rule out the possibility of PCR artifacts, two sets of primers were used to perform further PCR amplifications. Primers A and B (see Experimental Procedures, Primer Strategy) located in exons 1 and 3, respectively, amplified a DNA fragment that is about 150 bp longer from AS11 (FIG. 7b, lane 2) than that from the wild type (FIG. 7b, lane 1). The second pair of primers, C and B (Experimental Procedures), with one to be found in both exon 2 and the insertion segment, and the other located in exon 3, generated two amplified fragments from AS11 (FIG. 7b, lane 4), while only one from the wild type (FIG. 7b, lane 3). Hence these results confirmed that the insertion mutation the inventors identified through sequencing, reflected the true nature of the mutation in the TAG1 gene in the AS11 genome.

Example 5

The AS11 TAG1 Transcript has an 81-bp Insertion in Its Open Reading Frame

Northern blot analyses indicated that there was no difference in the expression profiles of the TAG1 gene, between the AS 11 mutant and wild type *A. thaliana*. In order to investigate the effect of the mutation at the transcript level, reverse-transcription PCR (RT-PCR) was performed to amplify the TAG1 transcript from RNA extracted from germinating seedlings of mutant AS11. Sequencing analysis revealed that there is an 81-bp insertion composed entirely of exon 2 in the transcript from AS11. The exon 2 in the repeat is properly spliced. The alteration of the transcript thus does not disturb the reading frame. However, this additional exon 2 sequence in the AS11 transcript would result in an altered DGAT protein with the 27 amino acid insertion $^{131}$SHAGLFNLCVVV-LIAVNSRLIIENLMK$^{157}$ (SEQ ID NO:11). The inventors' data shows that this insertion results in a 40-70% reduction in DGAT activity throughout seed development (Katavic et al., 1995). The 81 bp insert responsible for reduced DGAT activity in AS11 is visible in the comparison of RT-PCR products (FIG. 7b: Compare lane 5 (WT) and lane 6 (AS11).) The DNA aberration observed in the AS11 mutant was unexpected, since ethyl methanesulfonate (EMS) generally causes point mutations. Although we cannot rule out the possibility that this AS11 mutant was the result of a spontaneous mutation event, EMS-induced deletions and insertions have been reported in other systems (Mogami et al., 1986, Okagaki et al., 1991).

Example 6

The TAG1 Gene Insertion in *Arabidopsis* Mutant AS11 Affects Seed Triacylglycerol Accumulation, but not Sterol Ester Accumulation in Seeds Because TAG1 also showed some sequence homology to acyl CoA: cholesterol acyltransferases (ACATs) from a number of species (Chang et al., 1997), the inventors compared both triacylglycerol and sterol ester accumulation in seeds of the wild-type *A. thaliana* and AS11 mutant. While the triacylglycerol content and TAG/DAG ratios were reduced in AS11 (i.e. increased proportion of seed oil DAGs,) in contrast, the proportions of sterol esters in WT and AS11 seeds were similar, at 0.8 and 1% of the total lipid extract, respectively (Table 1). If the TAG1 lesion affected ACAT-like activity, one might expect a reduction in seed sterol esters, but this was not observed. These results indicated that TAG1 is not involved in sterol-ester homeogenesis, and thus not an acyl CoA: sterol acyltransferase.

Example 7

TAG1 Expression in Yeast

The TAG1 cDNA overexpressed in yeast resulted in a 3.5 to 4-fold increase in microsomal DGAT activity compared to plasmid only (pYES2) control transformants (FIG. 8), confirming that the TAG1 gene product functions as a DGAT. When $^{14}$C18:1-CoA was added to the yeast lysates, sterol esters were also labeled in vitro (data not shown), but there was no significant difference in the $^{14}$C-labeled sterol esters produced by lysates from the pYES2 GAL-induced control and the pYES2:TAG1 Gal-induced transformant. This confirms that the TAG1 product does not encode an acyl-CoA: sterol acyltransferase (like ACAT).

Example 8

Complementation of the *A. thaliana* AS11 Mutant Line by Transformation with the DGAT cDNA The cloned full-length DGAT cDNA was used as a template for PCR amplification with the primers DGATXbaI (CTAGTCTAGAATGGCGATTTTGGA; SEQ ID NO:12) and DGATXhoI (GCGCTCGAGTTTCATGACATCGA; SEQ ID NO:13) to provide new restriction sites on each end of the sequence as described in Experimental Procedures. A 1.6 kb fragment was excised by a XbaI/KpnI digestion and ligated into the corresponding sites of the pSE129 vector (provided by Dr. P. Covello, PBI/NRC). pSE129A is a vector derived from the plant transformation vector pRD400 (Datla et al. 1992). The vector pSE129A contains the seed-specific napin promoter and the nos terminator cloned into the EcoRI and HindIII sites of the pRD400 plasmid (FIG. 9). Hence in the DGAT-pSE129A construct, the *Arabidopsis* DGAT cDNA is under the control of the napin promoter. The construct integrity was confirmed by sequencing.

The pSE129A containing the napin:DGATcDNA was introduced into *A. tumefaciens*, used to transform *A. thaliana* mutant AS11, and progeny analyzed as described in Experimental Procedures. A number of $T_2$ transgenic lines were isolated which complemented the fatty acid mutant phenotype found in AS11 (reduced 20:1 and elevated polyunsaturated $C_{18}$s), restoring the wild-type seed fatty acid profile (FIG. 10). This finding confirms the nature of the lesion in AS11 and directly ties the AS11 lipid phenotype to this mutation.

Example 9

Over-Expression of the DGAT cDNA in Wild-Type *A. thaliana*

The cloned fill-length DGAT cDNA was used as a template for PCR amplification with the primers DGATXbaI (CTAGTCTAGAATGGCGATTTTGGA; SEQ ID NO:12) and DGATXhoI (GCGCTCGAGTTTCATGACATCGA: SEQ ID NO:13) to provide new restriction sites on each end of the sequence as described in Experimental Procedures. A 1.6 kb fragment was excised by a XbaI/KpnI digestion and ligated into the corresponding sites of the pSE129 vector (provided by Dr. P. Covello, PBI/(NRC). pSE129A is a vector derived from the plant transformation vector pRD400 (Datla et al. 1992). The vector pSE129A contains the seed-specific napin promoter and the nos terminator cloned into the EcoRI and HindIII sites of the pRD400 plasmid (FIG. 9). Hence in the DGAT-pSE129A construct, the *Arabidopsis* DGAT cDNA is under the control of the napin promoter. The construct integrity was confirmed by sequencing.

The pSE129A containing the napin:DGATcDNA was introduced into *A. tumefaciens*, used to transform wild-type *A. thaliana*, and progeny analyzed as described in Experimental Procedures. A number of $T_2$ transgenic lines were isolated which exhibited an increased oil content (FIG. 11) an increased average 100-seed weight (FIG. 12) and a strong linear correlation between the two traits (FIG. 13).

In terms of fatty acyl composition, wild type lines containing over-expressed DGAT cDNA showed a decrease in the total saturates, and increases in the monounsaturates and in the 18:1/[18:2+18:3] index, as shown in Table 2 below. Such changes are all towards a "healthier" oil profile, and can be applied directly to canola, other oilseeds in the Brassicaceae and other edible oil crops to produce similar oil composition improvements.

TABLE 2

Fatty acid composition of seed oil from *A. thaliana* non-transformed wild-type controls (WT Con) and three T2 transgenic lines (2', 9 and 11) of wild type transformed with the DGAT cDNA under the control of a napin promoter (napin: DGAT).

| Line | Total Saturates[a] Wt % | Monounsaturates[b] Wt % | 18:1/[18:2 + 18:3] index[c] |
|---|---|---|---|
| WTControl | 15.1 ± 0.1 | 36.7 ± 0.2 | 29.9 ± 0.6 |
| 2' napin:DGAT | 13.4 | 38.6 | 34.1 |
| 9 napin:DGAT | 13.1 | 39.3 | 35.6 |
| 11 napin:DGAT | 13.1 | 38.3 | 33.0 |

[a]Includes 16:0, 18:0, 20:0, 24:0
[b]includes 18:1, 20:1, 22:1, 24:1
[c]([Wt % 18:1] + [Wt % 18:2 + Wt % 18:3]) × 100

EXPERIMENTAL PROCEDURES

Example 10

Plant Material

*Arabidopsis thaliana* ecotype Columbia and mutant AS11 were grown under conditions described previously (Katavic et al., 1995). The *A. thaliana* mutant line AS11 was generated and characterized relative to wild type (WT) *A. thaliana* ecotype Columbia, as described by Katavic et al., (1995); (ATCC NO: PTA-1013).

Example 11

DNA Manipulation

Standard methods and procedures were used for DNA preparation, plasmid propagation and isolation (Sambrook et al., 1989). Sequencing was conducted on an Applied Biosystems Model 373A DNA Sequencing System using the Taq DyeDeoxy™ Terminator Cycle Sequencing Kit (Applied Biosystems, Inc.). The nucleotide and the deduced amino acid sequences were compared with sequences available in databanks using the BLAST program (Altschul et al., 1990).

Example 12

Southern and Northern Analysis

Total RNA was extracted from different tissues at various developmental stages, using the method of Lindstrom and Vodkin (1991). RNA samples were denatured with formaldehyde and separated on 1.2% formaldehyde-agarose gels. About 5 μg of total RNA was loaded, and the amount of RNA per lane was calibrated by the ethidium bromide-staining intensity of the rRNA bands. Genomic DNA was isolated, digested with restriction enzymes and a Southern blot analysis was performed according to Sambrook et al. (1989). The TAG1 DNA probe was $^{32}$P labeled by random-priming according to protocols of the manufacture (BRL).

Example 13

PCR Strategy

Primers used for the amplification of the TAG1 gene were as follows:

DGAT1 (AGACACGAATCCCATTCCCACCGA; SEQ ID NO:14),

DGAT2 (AGTGGTGACAACGCAGGGATGATG; SEQ ID NO:15),

DGAT3 (ATGGTCGCTCCCACATTGTGT; SEQ ID NO:16),

DGAT4 (CATACAATCCCCATGACATTTATCA; SEQ ID NO:17).

DGAT1 and DGAT2 amplify the 5' half of the TAG1 gene and DGAT3 and DGAT4 amplify the 3' end of the TAG1 gene. Genomic DNA from AS11 was used as template for PCR amplification of the mutant TAG1 allele using the thermal profile: 94° C. 3 min; 40 cycles of 94° C. 30 seconds, 62° C. 45 seconds, 72° C. 1 min; and 72° C. 15 min. To further confirm the mutation, primers A (CGACCGTCGGTTC-CAGCTCATCGG; (SEQ ID NO:18)) and B (GCGGC-CAATCTCGCAGCGATCTTG; (SEQ ID NO:19)), as well as primers C (TAAACAGTAGACTCATCATCG; (SEQ ID NO:20)) and B, were used in pairs, respectively, to amplify the internal fragment containing the mutation. The primers DGAT1 and DGAT4 were used for PCR amplification of the cDNA with an *A. thaliana* silique cDNA library as template. Primers A and B were also used in RT-PCR amplification of the cDNA fragment encompassing the insertion segment.

Example 14

Construction of TAG1 Multicopy Vector and Transformation and Characterization of DGAT Expression in Yeast The TAG1 cDNA was cloned into pBluescript SK as described (Hadjeb and Berkowitz, 1996). The cDNA was cut out from the vector with KpnI/XbaI, and subsequently cloned into the respective sites of the yeast expression vector pYes2 (Invitrogen). The construct was confirmed by sequencing. Constructs with TAG1 transcription under the control of the GAL1 promoter released a fragment of approximately 1.9 kb. Because the TAG1 fragment has its own initiating ATG codon, the product expressed is not a fusion protein. As a host for yeast expression, an SLC deletion strain (YMN5 [slc1Δ2::LEU2 ura3]) (kindly provided by M. M. Nagiec and R. C. Dickson, University of Kentucky, Lexington, Ky.; Nagiec et al., 1993) was used; we reasoned that in this mutant, the endogenous DAG pool may be lower than in WT yeast, and that this would allow us to maximize the activity from over-expressed TAG1 in the presence of exogenously supplied $^{14}$C-DAG during in vitro DGAT assays of transformant lysates. Yeast transformation was performed according to Elble (1992). YMN5 transformants containing vector only (pYES2) were used as controls. Single colonies were cultured overnight in 20 mL of SD medium (Synthetic Dextrose medium with glucose and without uracil, as described by Ausubel et al., 1995, Vol. 2, p. 13.1.3) on a rotary shaker (270 rpm) at 28° C. Cells were pelleted from the overnight culture and resuspended in 50 mL of medium for induction of expression (SD medium containing galactose and without uracil). Cells were reincubated at 28° C., with shaking at 270 rpm, and harvested after 4-6 hr. GAL-induced yeast transformants were harvested by centrifugation at 5000 rpm for 5 min and resuspended in 100 mM Hepes-NaOH, pH 7.4, containing 1 mM EDTA and 1 mM DTT. Cell lysates were prepared using acid-washed glass beads as described by Ausubel et al. (1995). Protein in yeast lysates was measured using the Bradford (1976) assay, protein levels in each lysate were normalized and aliquots (250 μg protein) were assayed for DGAT activity as described below.

Example 15

Lipid Substrates and DGAT Analyses $^{14}$C-labeled diolein [1-$^{14}$C oleic] (Sp. activity 55 mCi/mmol) was purchased from American Radiolabeled Chemicals (St. Louis, Mo.). The $^{14}$C-labeled sn-1,2-diolein isomer was purified by TLC on borate-impregnated plates and emulsified in Hepes buffer the presence of 0.2% Tween-20 as described by Taylor et al., (1991). 20:1-CoA, CoASH, ATP, and all other biochemicals were purchased from Sigma.

DGAT assays were conducted at pH 7.4, with shaking at 100 rpm in a water bath at 30° C. for 30-60 min. Assay mixtures (0.5 mL final volume) contained lysate protein (250 μg), 90 mM Hepes-NaOH, 0.5 mM ATP, 0.5 mM CoASH, 1 mM MgCl$_2$, 200 μM sn-1,2 diolein (sp. activity 2 nC/nmol) in 0.02% Tween 20, and 18 μM 20:1-CoA as the acyl donor. The $^{14}$C-labeled TAGs were isolated by TLC and quantified as described by Taylor et al (1991).

Example 16

Further Lipid and Sterol Ester Analyses in AS11 and WT

Total lipid extracts (TLEs), and lipid class analyses in WT and the AS11 mutant were performed as described by Taylor et al., (1991; 1992) and by Katavic et al., (1995). Relative seed oil content was also measured by magic angle sample spinning $^1$H-NMR, according to the method of Rutar (1989). Analyses were conducted with 200-seed samples of intact wild-type and AS11 seeds using a Bruker AM wide-bore spectrometer (Bruker Analytische Masstechnik GHBH, Silberstreifen D-76287, Rheinstetten4/Karlstuhe, Germany) operating at 360 MHz. To reduce anisotropic line broadening, the seed sample was rotated at 1 kHz in a zirconium rotor oriented 54.7° to the magnetic field. The integration response for resonances attributable to liquid-like oil were summed and the value for AS11 seed was recorded relative to the response for the WT control seed sample, the latter set at a value of 1.00.

Sterol esters were purified from the TLEs by thin layer chromatography (TLC) on Silica H plates developed in hexane:diethyl ether:formic acid (80:20:2, v/v/v). After elution from the silica H with chloroform:methanol (2:1, v/v), the sterol esters were quantified by saponification followed by methylation of the resulting fatty acids with 3N methanolic-HCl. The fatty acid methyl esters (FAMEs) were analyzed by GC as described previously (Taylor et al., 1991). The free sterols released by saponification were also analyzed by GC on a 30 m DB-5 column; GC temperature program: initial temp: 180° C., increasing at 10° C./min to 300° C. and held at this temperature for 15 min. The sterol ester content was reported as a % of the TLE; i.e. FAMEs released from sterol esters calculated as proportion of the FAMEs released by transmethylation of the total lipid extract (TLE).

Example 17

Construction of Plant Transformation Vector Containing the Wild-Type DGAT Gene for Over-Expression in WT *A. thaliana* and Complementation of the *A. thaliana* AS11 Mutant

```
Two primers:                           (SEQ ID NO:21)
Gen 1 (GAGAGGATCCACGCTCACGACCCATTCTTCCCG;), and
                                       (SEQ ID NO:22)
Gen 2 (AAGAAGGATCCATCCCCAAAACGGGACCACCAA)
``` were synthesized according to sequences upstream and downstream of the TAG1 gene. These primers were used to PCR amplify a genomic fragment of 5.1 kb from wild-type *A. thaliana*. The PCR fragment was purified and digested with BamHI and inserted into the corresponding site in plasmid pRD400 (Datla et al. 1992) to generate the plant transformation vector DGATg-pRD400.

Example 18

Construction of DGAT cDNA Plant Transformation Vector for Seed-Specific Expression The cloned full-length DGAT cDNA was used as a template for PCR amplification with the primers DGATXbaI (CTAGTCTAGAATGGCGATTTTGGA; SEQ ID NO:12) and DGATXhoI (GCGCTCGAGTTTCATGACATCGA; SEQ ID NO:13) to provide new restriction sites on each end of the sequence. The PCR profile was as follows: 94° C. 1 min; 30 cycles of 94° C. 30 seconds, 55° C. 30 seconds, 72° C. 1 min; and 72° C. 5 min. The PCR product was then ligated into the PCR-2.1 vector (InVitrogen). A 1.6 kb fragment was excised by a XbaI/KpnI digestion and ligated into the corresponding sites of the pSE129 vector (provided by Dr. P. Covello, PBI/NRC). pSE129A is a vector derived from the plant transformation vector pRD400 (Datla et al. 1992). The vector pSE129A contains the seed-specific napin promoter and the nos terminator cloned into the EcoRI and HindIII sites of the pRD400 plasmid (See FIG. 9). Hence in the DGAT-pSE129A construct, the *Arabidopsis* DGAT cDNA is under the control of the napin promoter. The construct integrity was confirmed by sequencing.

Example 19

Transformation of *Agrobacterium* with Plant DGAT Vector Construct

Electrocompetent *Agrobacterium* cells, GV3101 (pMP90) strain, were prepared as follows: An *Agrobacterium* culture was grown 24 to 48 hrs in 2YT, and when the absorbance at 600 nm reached 0.5 to 0.7, the cells were chilled on ice and pelleted by centrifugation (5,000×g, 10 min in a GSA rotor at 4° C.). The pellet was washed in 1, 0.5 and 0.02 volumes of cold 10% sterile glycerol and resuspended in 0.01 volume of cold 10% glycerol. The electrocompetent cells were then frozen in liquid N$_2$ and stored at −70° C. The *Agrobacterium* cells were transformed by electroporation with 20-50 ng of transforming DNA (either DGATg-pRD400 or DGAT-pSE129A) according to the manufacturer's instructions, plated on a selective medium (LB with 50 μg/mL kanamycin) and incubated overnight at 28° C. Single transformed cells were grown overnight (28° C., 225 r.p.m.) in 5 mL LB with 50 μg/mL Kanamycin and 25 μg/mL Gentamycin. DNA extraction and purification were performed with a Qiaprep Spin Miniprep kit (Qiagen). The fidelity of the construct was rechecked by DNA sequencing before plant transformation.

Example 20

Transformation of *Arabidopsis thaliana*

The transformation protocol was adapted from that described by Clough and Bent (1998). Seeds of *Arabidopsis thaliana* ecotype Columbia and mutant AS 11 (Katavic et al., 1995) were grown at 22° C. under fluorescent illumination (120 µE·m$^{-2}$.S$^{-1}$) in a 16 h light/8 hour dark regime. Typically, four to six plants were raised in a 10 cm$^2$ pot in moistened Terra-lite Redi-earth (W. R. Grace & Co. Canada Ltd. Ajax, ON, Canada). To prevent the soil mix in the pot from falling into the inoculation media, soil was mounded as a platform with seeds sown on top, and the whole pot covered by a nylon window screen and secured by a rubber band. Plants were vacuum infiltrated in an *Agrobacterium* suspension when the first flowers started opening.

To grow *Agrobacterium*, a 5 mL suspension in LB medium containing 50 µg/mL kanamycin and 25 µg/mL gentamycin was cultured overnight at 28° C. The day before infiltration, this "seed culture" was divided into four flasks containing 250 mL of LB medium supplemented with 50 µg/mL kanamycin and 25 µg/mL gentamycin. These cultures were grown overnight at 28° C. The next morning after the absorbance at 600 nm was checked (approximately =1.0), the cells were harvested by centrifugation (5,000×g, 10 min in a GSA rotor at room temperature) and resuspended in the infiltration medium (sucrose 5%; Silwet-77 0.005% in water) to obtain an optical density at 600 nm of 0.8.

The *Agrobacterium* suspension was poured into a beaker and the potted plants inverted into the beaker so that the flowers and bolts were submerged. The beaker was placed into a large Bell jar and a vacuum drawn using a vacuum pump, until bubbles formed on the stem surfaces and the solution started to bubble slightly, and then the vacuum was released rapidly. The necessary time and pressure will vary from one lab setup to the next, but good infiltration is visibly apparent as uniformly darkened, water-soaked tissue. Pots were removed from the beaker, laid on their side in a plastic tray and covered with a plastic dome, to maintain humidity. The following day, the plants were uncovered, set upright and allowed to grow for approximately four weeks in a growth chamber under continuous light conditions as described by Katavic et al., (1995). When the siliques were mature and dry, seeds were harvested and selected for positive transformants.

Example 21

Selection of Putative Transformants (Transgenic plants) and Analysis of Transgenic Plants For each construct, seeds were harvested in bulk. Seeds were surface-sterilized by submerging them in a solution containing 20% bleach and 0.01% Triton X-100 for 20 min, followed by three rinses with sterile water. Sterilized seeds were plated by resuspending them in sterile 0.1% phytagar at room temperature (about 1 mL phytagar for every 500-1000 seeds), and applying a volume containing 2,000-4,000 seeds onto 150×15 mm kanamycin selection plate. Plates were incubated for 2 days in the cold without light, and grown for 7-10 days in a controlled environment (22° C. under fluorescent illumination (120 µE·m$^{-2}$·s$^{-1}$) in a 16 h light/8 hour dark regime). The selection media contained ½ MSG medium, 0.8% phytagar, 3% sucrose, 50 1g/mL kanamycin and 50 µg/mL Timentin. Petri dishes and lids were sealed with a Micropore™ surgical tape (3M Canada, London, ON, Canada). After 7-10 days, drug-resistant plants that had green leaves and well established roots within the medium were identified as transformants and at the 3-5 leaf stage, selected transformants were transplanted into flats filled with heavily moistened soil mix. Transformants were grown to maturity and mature seeds (T$_2$ generation as defined in Katavic et al., (1994)) were harvested from individual plants, and further analyzed.

Genomic DNA was isolated from individual T$_1$ plants following the protocol of Dellaporta et al., (1983). A PCR amplification using the paired primers described previously for the DGAT cDNA or for the DGAT gene, was performed to confirm the presence of the cDNA or the gene, respectively, in the T$_1$ transformants. Southern analyses (Southern, 1975) were performed to select the transformants containing a single copy of the inserted fragment. DNA samples were digested with restriction enzymes (BglII for the DGAT cDNA and EcoRI for the DGAT gene), resolved by electrophoresis on a 1% agarose gel, and Southern blotting performed using a nylon filter (Hybond-N+, Amersham) according to Sambrook et al. (1989). The DGAT cDNA fragment, labeled with α-[$^{32}$P] dCTP (NEN/DuPont) using the Random Primer DNA labeling kit (Gibco BRL), was used as a probe. Hybridization was performed at 60° C. according to Church and Gilbert (1984). The filter was then exposed to Kodak X-OMAT-AR film.

DEPOSIT INFORMATION

The following biological material has been deposited at the American Type Culture Collection (ATCC) of 10801 University Boulevard, Manassas, Va., 20110-2209, U.S.A. All of these deposits were made on behalf of the Applicant/Assignee (National Research Council of Canada) under the terms of the Budapest Treaty on the dates indicated, and have been given the accession numbers shown below.

| Deposited Material | Date of Deposit | Accession No. |
| --- | --- | --- |
| *Arabidopsis* DGAT gene | Nov. 29, 1999 | PTA-988 |
| *Arabidopsis* DGAT cDNA | Nov. 29, 1999 | PTA-989 |
| *Arabidopsis* AS11 seeds | Dec. 3, 1999 | PTA-1013 |

SEQUENCE LISTING FREE TEXT

The Sequence Listing provided below contains free text entries in respect of SEQ ID NOs:12 to 22. The free text used in the Sequence Listing is repeated as follows:

| | |
| --- | --- |
| SEQ ID NO: 12 | Primer of DGATXbaI |
| SEQ ID NO: 13 | Primer of DGATXhoI |
| SEQ ID NO: 14 | Primer DGAT1 |
| SEQ ID NO: 15 | Primer DGAT2 |
| SEQ ID NO: 16 | Primer DGAT3 |
| SEQ ID NO: 17 | Primer DGAT 4 |
| SEQ ID NO: 18 | Primer A |
| SEQ ID NO: 19 | Primer B |
| SEQ ID NO: 20 | Primer C |
| SEQ ID NO: 21 | Primer Gen 1 |
| SEQ ID NO: 22 | Primer Gen 2. |

A summary of all of the listed sequences is provided below for ease of review:

SEQ ID NO:1—(pDGAT; vector containing isolated and purified deoxyribonucleic acid cDNA; ATCC No PTA-989), Genbanl/EMBL Accession No. AJ238008.

SEQ ID NO:2—The deduced amino acid sequence of the *Arabidopsis* DGAT (AtTAG1) protein.

SEQ ID NO:3—(pgenomic DGAT; vector containing isolated and purified genomic deoxyribonucleic acid (genomic DNA) ATCC No PTA-988).

SEQ ID NO:4—MDGAT, mouse DGAT [GenBank/EMBL Accession No. AF078752 (Cases et al., 1998)].

SEQ ID NO:5—HARGP1, human ARGP1 protein [GenBank/EMBL Accession No. AF059202; Oelkers et al., 1998].

SEQ NO:6—*Arabidopsis thaliana* expressed sequence tag (EST) [accession no. AA042298].

SEQ ID NO:7—A diacylglycerol/phorbol ester-binding motif found in SEQ ID NO:2, SEQ ID NO:8 and SEQ ID NO:9 ($^{414}$HKWMVRHIYFP$^{424}$).

SEQ ID NO:8—*B. napus* DGAT amino acid sequence GenBank EMBL Accession No AF155224.

SEQ ID NO:9—*B. napus* DGAT amino acid sequence GenBank/EMBL Accession No. AF164434.

SEQ ID NO:10—Targeting motif typical of members of the SnRK1 protein kinase family found in SEQ ID NO:2, SEQ ID NO:8 and SEQ ID NO:9 X-L$^{200}$-X-K$^{202}$-X-X-S$^{205}$-X-X-X-V$^{209}$ SEQ ID NO:11—A 27 amino acid insertion repeat in SEQ ID NO:2 found in the *Arabidopsis thaliana* AS11 mutant.

$^{131}$SHAGLFNLCVVVLIAVNSRLIIENLMK$^{157}$

SEQ ID NO:12—CTAGTCTAGAATGGCGATTTGGA (nucleotide sequence of Primer DGATXbaI).

SEQ ID NO:13—GCGCTCGAGTTTCATGACATCGA (nucleotide sequence of Primer DGATXhoI).

SEQ ID NO:14—AGACACGAATCCCATTCCCAC-CGA (nucleotide sequence of Primer DGAT1).

SEQ ID NO:15—AGTGGTGACAACGCAGGGAT-GATG (nucleotide sequence of Primer DGAT2).

SEQ ID NO:16—ATGGTCGCTCCCACATTGTGT (nucleotide sequence of Primer DGAT3).

SEQ ID NO:17—CATACAATCCCCATGACATTTATCA (nucleotide sequence of Primer DGAT4).

SEQ ID NO:18—CGACCGTCGGTRCCAGCT-CATCGG (nucleotide sequence of Primer A).

SEQ ID NO:19—GCGGCCAATCTCGCAGC-GATCTTG (nucleotide sequence of Primer B).

SEQ ID NO:20—TAAACAGTAGACTCATCATCG (nucleotide sequence of Primer C).

SEQ ID NO:21—GAGAGGATCCACGCTCACGAC-CCATTCTTCCCG (nucleotide sequence of primer Gen 1).

SEQ ID NO:22—AAGAAGGATCCATC-CCCAAAACGGGACCACCAA (nucleotide sequence of primer Gen 2).

SEQ ID NO:23—AS11 mutant DGAT cDNA nucleotide sequence.

SEQ ID NO:24—AS11 mutant DGAT genomic DNA nucleotide sequence.

SEQ ID NO:25—the deduced amino acid sequence of SEQ ID NO:23.

SEQ ID NO:26—A putative diacylglycerol/phorbol ester-binding motif found in SEQ ID NO:2, SEQ ID NO:7, SEQ ID NO:8 and SEQ ID NO:9

REFERENCES

Altschul, S. F., Gish, W., Miller, W., Myers, E. W. and Lipman, D. J (1990) Basic local alignment search tool. *J. Mol. Biol.* 215, 403-410.

Ausubel, F. M., Brent, R., Kingston, R. E., Moore, D. D., Seidman, J. G., Smith, J. A., and Stuhl, K., eds (1995). Current Protocols in Molecular Biology, Vols 1, 2, and 3. Wiley, New York.

Bechtold, N., Ellis, J., and Pelletier, G. (1993) In planta *Agrobacterium*-mediated gene transfer by infiltration of adult *Arabidopsis thaliana* plants. *C R Acad Sci Paris, Sciences de la vie/Life sciences* 316: 1194-1199.

Becker, D., Brettschneider, R. and Lörz, H. (1994) Fertile transgenic wheat from microprojectile bombardment of scutellar tissue. Plant J. 5: 299-307.

Bernerth R, Frentzen M (1990) Utilization of erucoyl-CoA by acyltransferases from developing seeds of *Brassica napus* (L.) involved in triacylglycerol biosynthesis. *Plant Sci* 67: 21-28.

Bradford M. M. (1976). A rapid and sensitive method for the quantitation of microgram quantities of protein utilizing the principle of protein-dye binding. Anal. Biochem. 72, 248-254.

Budziszewski, G. J., Croft, K. P. C. and Hildebrand, D. F. (1996) Uses of biotechnology in modifying plant lipids. Lipids 31: 557-569.

Cao, Y-Z and Huang, AHC (1986) Diacylglycerol acyltransferase in maturing oil seeds of maize and other species. *Plant Physiol.* 82: 813-820.

Cao Y-Z, Huang A H C (1987) Acyle coenzyme A preference of diacylglycerol acyltransferase from maturing seeds of *Cuphea*, maize, rapeseed and canola. *Plant Physiol.* 84: 762-765

Cases, S., Smith, J. S., Zheng, Y-W., Myers, H. M., Lear, S. R., Sande, E., Novak, S., Collins, C., Welch, C. B., Lusis, A. J., Erickson, S. K. and Farese, R. V., JR. (1998) Identification of a gene encoding a acyl CoA: diacylglycerol acyltransferase, a key enzyme in triacylglycerol synthesis. *Proc. Nat'l. Acad. Sci. USA*, 95, 13018-13023.

Chang, T. Y., Chang, C. C. Y. and Cheng, D. (1997) Acyl-Coenzyme A: Cholesterol Acyltransferase. Annu. Rev. Biochem. 66, 613-38.

Church, G. M. and Gilbert, W. (1984) Genomic sequencing. Proc. Natl. Acad. Sci. USA. 81, 1991-95.

Clough, S. J. and Bent, A. F. (1998) Floral dip: a simplified method for *Agrobacterium*-mediated transformation of *Arabidopsis thaliana*. The Plant Journal 16, 735-43

Datla, R. S. S., Hammerlindl, J. K., Panchuk, B., Pelcher, L. E. and Keller, W. A. (1992) Modified binary plant transformation vectors with the wild-type gene encoding NPTII. Gene 211: 383-384.

Datla, R. S. S., Bekkaoui, F., Hammerlindl, J., Pilate, G., Dunstan, D. I. and Crosby, W. L. (1993) Improved high-level constitutive foreign gene expression in plants using an AMV RNA4 untranslated leader sequence. *Plant Sci.* 94: 139-149.

Datla, R., Anderson, J. W. and Selvaraj, G. (1997) Plant promoters for transgene expression. Biotechnology Annual Review 3: 269-296.

DeBlock, M., DeBrouwer, D. and Tenning P. (1989) Transformation of *Brassica napus* and *Brassica oleracea* using *Agrobacterium tumefaciens* and the expression of the bar and neo genes in the transgenic plants. *Plant Physiol.* 91: 694-701.

De Lange, P., Van Blokland, R., Kooter, J. M. and Mol, J. M. N. (1995) Suppression of flavenoid flower pigmentation genes in *Petunia hybrida* by the introduction of antisense and sense genes. In: Gene Silencing in Higher Plants and Related Phenomena in Other Eukaryotes. P. Meyer (Ed.), Springer-Verlag, Berlin, pp. 55-75.

Dellaporta, S. L., Wood, J. and Hicks, J. B. (1983) A plant DNA minipreparation:Version II. Plant Mol. Biol. Rep. 1, 19-21

Elble, R. (1992). A simple and efficient procedure for transformation of yeasts. *Biotechniques* 13, 18-20.

Focks, N. and Benning, C. (1998) wrinkled1: A novel, low-seed-oil mutant of *Arabidopsis* with a deficiency in the seed-specific regulation of carbohydrate metabolism. *Plant Physiol.* 118, 91-101.

Frentzen M (1993) Acyltransferases and triacylglycerols. In: Moore, Jr. TS, editor, *Lipid Metabolism in Plants*, pp. 195-230. CRC Press, Ann Arbor,.

Giraudat, J., Hauge, B. M., Valon, C., Smalle, J., Parcy, F., Goodman, H. M. (1992) Isolation of the *Arabidopsis* AB13 gene by positional cloning. *Plant Cell* 4, 1251-1261.

Goodman, H. M., Ecker, J. R. and Dean, C. (1995) The genome of *Arabidopsis thaliana. Proc. Nat'l. Acad. Sci. USA* 92: 10831-10835.

Hadjeb N and Berkowitz G A (1996) Preparation of T-overhang vectors with high PCR product cloning efficiency. *Biotechniques* 20: 21-22.

Halford, N. G. and Hardie, D. G. (1998) SNF1-related protein kinases: global regulators of carbon metabolism in plants? *Plant Mol. Biol.* 37, 735-748.

Hitz, W. D., Mauvis, C. J., Ripp, K. G., Reiter, R. J., DeBonte, L. and Chen, Z. (1995) The use of cloned rapeseed genes for cytoplastic fatty acid desaturases and the plastid acyl-ACP thioesterases to alter relative levels of polyunsaturated and saturated fatty acids in rapeseed oil. Proc. 9th International Cambridge Rapeseed Congress UK, pp. 470-472.

Ichihara, K. and Noda, M. (1981) Lipid synthesis in germinating safflower seeds and protoplasts. *Phytochemistry* 20, 1245-1249.

Ichihara, K., Takahashi, T. and Fujii, S. (1988) Diacylglycerol acyltransferase in maturing safflower seeds: its influences on the fatty acid composition of the triacyiglycerol and on the rate of triacylglycerol synthesis. *Biochim. Biophys. Acta* 958, 125-129.

Jorgensen, R. A. and Napoli, C. A. (1994) Genetic engineering of novel plant phenotypes. U.S. Pat. No. 5,283,184.

Josefsson, L-G, Lenman M, Ericson M L and Rask L (1987) Structure of a gene encoding the 1.7S storage protein, napin, from *Brassica napus. J biol Chem* 262: 12196-12201.

Katavic, V., Haughn, G. W., Reed, D., Martin, M. and Kunst, L. (1994) In planta transformation of *Arabidopsis thaliana. Mol. Gen. Genet.* 245: 363-370.

Katavic, V., Reed, D. W., Taylor, D. C., Giblin, E. M., Barton, D. L., Zou, J-T., MacKenzie, S. L., Covello, P. S. and Kunst, L. (1995) Alteration of fatty acid composition by an EMS-induced mutation in *Arabidopsis thaliana* affecting diacylglycerol acyltransferase activity. Plant Physiol. 108, 399-409.

Kinney, A. J. (1995) Improving soybean seed quality. In: Induced Mutations and Molecular Techniques for Crop Improvement. International Atomic Energy Agency, Vienna, Austria., pp. 101-113.

Kinney, A. J. (1997) Genetic engineering of oilseeds for desired traits. In: Genetic Engineering, Vol. 19 (J. K. Setlow, ed.), Plenum Press, NY., pp. 149-166.

Kishore G. M. and Somerville, C. R. (1993) Genetic engineering of commercially useful biosynthetic pathways in transgenic plants. Current Opinion in Biotechnology. 4: 152-158.

Knutzon, D. S., Thompson, G. A., Radke, S. E., Johnson, W. B., Knauf, V. C., and Kridl, J. C. (1992) Modification of Brassica seed oil by anti-sense expression of a stearoylacyl carrier protein desaturase gene. Proc. Nat'l Acad. Sci. USA, 89: 2624-2628.

Knutzon, D. S., Lardizabal, K. D., Nelson, J. S., Bleibaum, J. L., Davis, H. M and Metz, J. (1995) Cloning of a coconut endosperm cDNA encoding a 1-acyl-sn-glycerol-3-phosphate acyltransferase that accepts medium chain length substrates. Plant Physiol. 109, 999-1006.

Kwanyuen, P. and Wilson, R. F. (1986) Isolation and purification of diacylglycerol acyltransferase from germinating soybean cotyledons. Biochim. Biophys. Acta 877, 238-245.

Lacey D J, Hills M J (1996) Heterogeneity of the endoplasmic reticulum with respect to lipid synthesis in developing seeds of *Brassica napus L*. Planta 199: 545-551.

Lagercrantz, U., Putterill, J., Coupland, G. and Lydiate, D. (1996) Comparative mapping in *Arabidopsis* and *Brassica*, fine scale genome collinearity and congruence of genes controlling flowering. Plant J. 9:13-20.

Lassner, M. W., Levering, C. K., Davis, H. M. and Knutzon, D. S. (1995) Lysophosphatidic acid acyltransferase from meadowfoam mediates insertion of erucic acid at the sn-2 position of triacylglycerol in transgenic rapeseed oil. Plant Physiol. 109, 1389-1394.

Lassner, M. W., Lardizabal, K, and Metz, J. G. (1996) A jojoba β-ketoacyl-CoA synthase cDNA complements the canola fatty acid elongation mutation in transgenic plants. The Plant Cell, 8: 281-292.

Lewin T M, Wang P and Coleman R A (1999) Analysis of amino acid motifs diagnostic for the sn-glycerol-3-phosphate acyltransferase reaction. Biochemistry 38: 5764-5771.

Lindstrom J. T. and Vodkin L. O. (1991) A soybean cell wall protein is affected by seed color genotype. Plant Cell 3:561-571

Little D, Weselake R J, Pomeroy M K, Furukawa-Stoffer T and Bagu J (1994) Solubilization and characterization of diacylglycerol acyltransferase from microspore-derived cultures of oilseed rape. Biochem J 304: 951-958.

Lloyd, A. M., Walbot, V. and Davis, R. W. (1992) *Arabidopsis* and *Nicotiana* anthocyanin production activated by maize regulators Rand C1. Science 258: 1773-1775.

MacKenzie, S. L. and Jain, R. K. (1997) Improvement of oils crops via biotechnology. Recent Res. Dev. In Oil Chem. 1:149-158.

Mayorek, N, Grinstein I, and Bar-Tana J (1989) Triacylglycerol synthesis in cultured rat hepatocytes. The rate-limiting role of diacylglycerol acyltransferase. Eur J Biochem 182: 395-400.

Meyer, P. (1995) Understanding and controlling transgene expression. Trends in Biotechnology, 13: 332-337.

Meyerowitz, E. M. (1987) *Arabidopsis thaliana*. Ann. Rev. Genet. 21: 93-111.

Meyerowitz, E. M. and Chang, C. (1985) Molecular biology of plant growth and development: *Arabidopsis thaliana* as an experimental system. In: Developmental Biology, Vol. 5, Plenum Press, NY., pp. 353-366.

Mogami, K., O'Donnell, P. T., Bernstein, S. I., Wright, T. R. F and Emerson, C. P., JR. (1986) Mutations of the *Drosophila* myosin heavy-chain gene: effects on transcription, Mol, J. M. N., Van der Krol, A. R., Van Tunen, A. J., Van Blokland, R., De Lange, P. and Stuitje, A. R. (1990) Regulation of plant gene expression by antisense RNA. FEBS Lett. 268: 427-430.

Moloney, M. M., Walker, J. M. and Sharma, K. K. (1989) High efficiency transformation of *Brassica napus* using *Agrobacterium* vectors. Plant Cell Rep. 8: 238-242.

Nagiec, M. M., Wells, G. B., Lester, R. L., and Dickson, R. C. (1993). A suppressor gene that enables *Saccharomyces cerevisiae* to grow without making sphingolipids encodes a protein that resembles an *Escherichia coli* fatty acyltransferase. J. Biol. Chem. 268, 22156-22163.

Nehra, N. S., Chibbar, R. N., Leung, N., Caswell, K., Mallard, C., Steinhauer, L. Baga, M. and Kartha K. K. (1994) Self-fertile transgenic wheat plants regenerated from isolated scutellar tissues following microprojectile bombardment with two distinct gene constructs. Plant J. 5: 285-297.

Nykiforuk C, Laroche A and Weselake RJ (1999) Isolation and sequence analysis of a novel cDNA encoding a putative diacylglycerol acyltransferase from a microspore-derived cell suspension culture of *Brassica napus* L. cv Jet Neuf (Accession No. AF155224).), Plant Physiology 120: PGR99-123.

Oelkers, P., Behar, A., Cromley, D., Billheimer, J. T. and Sturley, S. T. (1998) Characterization of two human genes encoding acyl Coenzyme A: cholesterol acyltransferase-related enzymes. J. Biol. Chem. 273, 26765-26771.

Okagaki, R. J., Neuffer, M. G. and Wessler, S. R. (1991) A deletion common to two independently derived Waxy mutations in maize. Genetics 128, 425-431.

Okuley, J., Lightner, J., Feldmann, K., Yadav, N., Lark, E. and Browse, J. (1994) *Arabidopsis* fad2 gene encodes the enzyme that is essential for polyunsaturated lipid synthesis. The Plant Cell 6:147-158.

Perry, H. Y. and Harwood, J. L. (1993a) Changes in the lipid content of developing seeds of *Brassica napus*. Phytochemistry 32: 1411-1415.

Perry, H. Y. and Harwood, J. L. (1993b) Use of [2-3H] glycerol precursor in radiolabeling studies of acyl lipids in developing seeds of *Brassica napus*. Phytochemistry 34: 69-73.

Poirier, Y., Dennis D E, Klomparens K and Somerville C (1992) Polyhydroxybutyrate, a biodegradable thermoplastic produced in transgenic plants. Science 256: 520-523.

Poirier, Y., Nawrath C and Somerville C (1995) Production of polyhydroxyalkanoates, a family of biodegradeable plastics and elastomers in bacteria and plants butyrate, a biodegradable thermoplastic produced in transgenic plants. Bio-Technology, 13: 142-150.

Poirier, Y., Ventre, G and Caldelari, D(1999) Increased flow of fatty acids toward β oxidation in developing seeds of *Arabidopsis* deficient in diacylglycerol acyltransferase activity or synthesizing medium-chain-length fatty acids. Plant Physiology 121: 1359-1366.

Potrykus, I. (1991) Gene transfer to plants: Assessment of published approaches and results. Annu. Rev. Plant Physiol. Plant Mol. Biol. 42: 205-225.

Radke S E, Andrews B M, Moloney M M, Crouch M L, Kridl J C, and KnaufVC (1988) Transformation of *Brassica napus L.* using *Agrobacterium tumefaciens*: developmentally regulated expression of a reintroduced napin gene. Theor. Appl. Genet. 75: 685-694.

Rhodes, C. A., Pierce, D. A., Mettler, I. J., Mascarenhas, D. and Detmer, J. J. (1988) Genetically transformed maize plants from protoplasts. Science 240: 204-207.

Rutar, V. (1989) Magic angle sample spinning NMR spectroscopy of liquids as a nondestructive method for studies of plant seeds. J. Agric. Food. Chem. 37, 67-70.

Sambrook J., Fritsch E. F. and Maniatis T. (1989) In Molecular Cloning, A Laboratory Manual, 2nd edition. Cold Spring Harbor Laboratory Press.

Sanford, J. C., Klein, T. M., Wolf, E. D. and Allen, N. (1987) Delivery of substances into cells and tissues using a particle bombardment process. J. Part. Sci. Technol. 5: 27-37.

Settlage, S H, Wilson R F and Kwanyuen, P. (1995) Localization of diacylglycerol acyltransferase to oil body associated endoplasmic reticulum. Plant Physiol. Biochem. 33: 399-407.

Shimamoto, K., Terada, R., Izawa, T. and Fujimoto, H. (1989) Fertile transgenic rice plants regenerated from transformed protoplasts. Nature 338: 274-276. Somerville, C. R. (1993) Future prospects for genetic modification of the composition of edible oils from higher plants. Am. J. Clin. Nutr. 58 (2 Suppl.): 270S-275S.

Songstad, D. D., Somers, D. A. and Griesbach, R. J. (1995) Advances in alternative DNA delivery techniques. Plant Cell, Tissue and Organ Culture 40:1-15.

Southern E. M. (1975) Detection of specific sequences among DNA fragments separated by gele electrophoresis. J. Mol. Biol. 98: 503-517.

Sparace S. A., Kleppinger-Sparace K. F., Stahl R. J., Xue L. and Qi, Q. (1992) Lipid biosynthesis in pea root plastids and some effects of glycolytic intermediates. In SL MacKenzie and DC Taylor, eds. Seed Oils for the Future, AOCS Press, Champaign, Ill. pp 52-60.

Stark, D. M., Timmerman, K. P., Barry, G. F., Preiss, J. and Kishore, G. M. (1992) Regulation of the amount of starch in plant tissues by ADP glucose pyrophosphorylase. Science 258: 287-292.

Stobart A K, Stymne S, Hǵlund S. (1986) Safflower microsomes catalyse oil accumulation in vitro: A model system. Planta 169: 33-37.

Stymne, S. and Stobart, A. K. (1987) Triacylglycerol Biosynthesis. In Stumpf, P. K. ed, The Biochemistry of Plants, Academic Press, New York. 9, 175-214.

Taylor. CB. (1998) Comprehending cosuppression. The Plant Cell 9:1245-1249.

Taylor, D. C., Weber, N., Barton, D. L., Underhill, E. W., Hogge, L. R., Weselake, R. J. and Pomeroy, M. K. (1991) Triacylglycerol bioassembly in microspore-derived embryos of *Brassica napus L.* cv. Reston. Plant Physiol. 97, 65-79.

Taylor, D. C., Barton, D. L., Rioux, K. P., MacKenzie, S. L., Reed, D. W., Underhill, E. W., Pomeroy, M. K. and Weber, N. (1992) Biosynthesis of acyl lipids containing very-long chain fatty acids in microspore-derived embryos of *Brassica napus L*. cv. Reston. Plant Physiol. 99, 1609-1618.

Tijburg, L B, Geelen, M J and van Golde L M (1989) Regulation of the biosynthesis of triacylglycerol, phosphatidylcholine and phosphatidylethanloamine in the liver. Biochim BiophysActa 1004:1-19.

Tzen T C, Cao Y, Laurent P, Ratnayake C and Huang H C (1993) Lipids, proteins and structures of seed oil bodies from diverse species. Plant Physiol. 101: 267-276.

Vasil, I. K. (1994) Molecular improvement of cereals. Plant Mol. Biol. 25: 925-937.

Vaucheret, H., Beclin C, Elmayan T, Feuerbach, F., Godon C, Morel J-B, Mourrain, P., Palauqui, J-C and Vernhettes S (1998) Transgene-induced gene silencing in plants. The Plant Journal 16: 651-659.

Voelker, T. A., Worrell, A. C., Anderson, L., Bleibaum, J., Fan, C., Hawkins, D. J., Radke, S. E., and Davies, H. M.

(1992) Fatty acid biosynthesis redirected to medium chains in transgenic oilseed plants. Science 257: 72-74.

Voelker, T. A., Hayes, T. R., Cramner, A. M., Turner, J. C., and Davies, H. M. (1996) Genetic engineering of a quantitative trait: metabolic and genetic parameters influencing the accumulation of laurate in rapeseed. The Plant Journal 9: 229-241.

Vogel, G and Browse, J (1996) Cholinephosphotransferase and diacylglycerol acyltransferase: Substrate specificities at a key branch point in seed lipid metabolism. Plant Physiol. 110: 923-931.

Walden, R. and Wingender, R. (1995) Gene-transfer and plant regeneration techniques. Trends in Biotechnology 13: 324-331.

Weselake, R. J., Taylor, D C, Pomeroy, M. K., Lawson S L, and Underhill E W (1991) properties of diacylglycerol acyltransferase from microspore-derived embryos of *Brassica napus L*. Photochemistry: 30: 3533-3538.

Weselake, R. J., Pomeroy, M. K., Furukawa, T. L., Golden, J. L., Little, D. B. and Laroche, A. (1993) Developmental profile of diacylglycerol acyltransferase in maturing seeds of oilseed rape and safflower and micro-spore-derived cultures of oilseed rape. Plant Physiol. 102, 565-571.

Wilson, R. F. and Kwanyuan P. (1986) Triacylglycerol synthesis and metabolism in germinating soybean cotyledons. Biochim. Biophys. Acta 877, 231-237.

Yang, H., Bard, M., Bruner, D. A., Gleeson, A., Deckelbaum, R. J., Aljinovic, G., Pohl, T. M., Rothstein, R. and Sturley, S. L. (1997) Sterol esterification in yeast: a two-gene process. Science 272, 1353-1356.

Yu, C., Kennedy, N. J., Chang, C. C. Y. and Rothblatt, J. A. (1996) Molecular cloning and characterization of two isoforms of *Saccharomyces cerevisiae* Acyl-CoA: Sterol Acyltransferase. J. Biol. Chem. 271, 24157-24163.

Zou, J-T., Katavic, V., Giblin, E. M., Barton, D. L., MacKenzie, S. L., Keller, W. A., Hu, X. and Taylor, D. C. (1997) Modification of seed oil content and acyl composition in the Brassicaceae by expression of a yeast sn-2 acyltransferase gene. The Plant Cell 9: 909-923.

The teachings of the above references are hereby incorporated by reference.

What is claimed is:

1. A process for producing a plant, plant seed or progeny thereof, the process comprising:
transforming a plant cell with a nucleic acid sequence encoding a diacylglycerol acyltransferase protein, wherein the nucleic acid sequence comprises the sequence according to SEQ ID NO: 1; growing a plant from the plant cell until the plant produces seed; and harvesting the seed from the plant, wherein the seed comprise the nucleic acid sequence.

2. The process of claim 1, wherein the nucleic acid sequence encoding the diacylglycerol acyltransferase protein is integrated into the genome of the plant cell.

3. The process of claim 1, further comprising selecting the seed having the nucleic acid sequence encoding the diacylglycerol acyltransferase protein integrated into the genome of the plant cell.

4. The process of claim 1, wherein the diacylglycerol acyltransferase protein comprises SEQ ID NO:2.

5. The process of claim 1, further comprising:
planting the seed in soil;
growing a second plant from the seed; and
harvesting the seed from the second plant, wherein the seed comprise the nucleic acid sequence.

6. The process of claim 1, wherein transforming the plant cell with the nucleic acid sequence encoding the diacylglycerol acyltransferase protein comprises:
transforming an *Agrobacterium* cell with the nucleic acid sequence encoding the diacylglycerol acyltransferase protein; and
transforming the plant cell with the *Agrobacterium* cell.

7. The process of claim 3, wherein selecting the seed having the nucleic acid sequence encoding the diacylglycerol acyltransferase protein integrated into the genome of the plant cell comprises:
isolating genomic nucleic acid from the seed; and
amplifying the nucleic acid sequence encoding the diacylglycerol acyltransferase protein from the isolated genomic nucleic acid from the seed.

8. The process of claim 1, wherein the plant is selected from the group consisting of *Arabidopsis thaliana, Borago* spp., Canola, *Ricinus* spp., *Theobroma* spp., *Zea* spp., *Gossypium* spp, *Crambe* spp., *Cuphea* spp., *Linum* spp., *Lesquerella* spp., *Limnanthes* spp., Linola, *Tropaeolum* spp., *Oenothera* spp., *Olea* spp., *Elaeis* spp., *Arachis* spp., rapeseed, *Carthamus* spp., *Glycine* spp., *Soja* spp., *Helianthus* spp., *Nicotiana* spp., *Vernonia* spp., *Triticum* spp., *Hordeum* spp., *Oryza* spp., *Avena* spp., *Sorghum* spp., *Secale* spp., Brassicaceae, and other members of the plant family Gramineae.

9. The process according to claim 1, further comprising extracting oil from the harvested seed.

* * * * *

SEQUENCE LISTING

<160> NUMBER OF SEQ ID NOS: 26

<210> SEQ ID NO 1
<211> LENGTH: 1904
<212> TYPE: DNA
<213> ORGANISM: Arabidopsis thaliana

<400> SEQUENCE: 1

```
atttcttagc ttcttccttc aatccgctct ttccctctcc attagattct gtttcctctt    60
tcaatttctt ctgcatgctt ctcgattctc tctgacgcct cttttctccc gacgctgttt   120
cgtcaaacgc ttttcgaaat ggcgattttg gattctgctg gcgttactac ggtgacggag   180
aacggtggcg gagagttcgt cgatcttgat aggcttcgtc gacggaaatc gagatcggat   240
tcttctaacg gacttcttct ctctggttcc gataataatt ctccttcgga tgatgttgga   300
gctcccgccg acgttaggga tcggattgat tccgttgtta acgatgacgc tcagggaaca   360
gccaatttgg ccggagataa taacggtggt ggcgataata acggtggtgg aagaggcggc   420
ggagaaggaa gaggaaacgc cgatgctacg tttacgtatc gaccgtcggt tccagctcat   480
cggagggcga gagagtcc acttagctcc gacgcaatct tcaaacagag ccatgccgga   540
ttattcaacc tctgtgtagt agttcttatt gctgtaaaca gtagactcat catcgaaaat   600
cttatgaagt atggttggtt gatcagaacg gatttctggt ttagttcaag atcgctgcga   660
gattggccgc ttttcatgtg ttgtatatcc ctttcgatct ttcctttggc tgcctttacg   720
gttgagaaat tggtacttca gaaatacata tcagaacctg ttgtcatctt tcttcatatt   780
attatcacca tgacagaggt tttgtatcca gtttacgtca ccctaaggtg tgattctgct   840
tttttatcag gtgtcacttt gatgctcctc acttgcattg tgtggctaaa gttggtttct   900
tatgctcata ctagctatga cataagatcc ctagccaatg cagctgataa ggccaatcct   960
gaagtctcct actacgttag cttgaagagc ttggcatatt tcatggtcgc tcccacattg  1020
tgttatcagc caagttatcc acgttctgca tgtatacgga aggttgggt ggctcgtcaa  1080 tttgcaaaac tggtcatatt caccggattc atgggattta taatagaaca atatataaat  1140
cctattgtca ggaactcaaa gcatcctttg aaaggcgatc ttctatatgc tattgaaaga  1200
```

-continued

```
gtgttgaagc tttcagttcc aaatttatat gtgtggctct gcatgttcta ctgcttcttc    1260
cacctttggt taaacatatt ggcagagctt ctctgcttcg gggatcgtga attctacaaa    1320
gattggtgga atgcaaaaag tgtgggagat tactggagaa tgtggaatat gcctgttcat    1380
aaatggatgg ttcgacatat atacttcccg tgcttgcgca gcaagatacc aaagacactc    1440
gccattatca ttgctttcct agtctctgca gtctttcatg agctatgcat cgcagttcct    1500
tgtcgtctct tcaagctatg gcttttcttt gggattatgt ttcaggtgcc tttggtcttc    1560
atcacaaact atctacagga aaggtttggc tcaacggtgg ggaacatgat cttctggttc    1620
atcttctgca ttttcggaca accgatgtgt gtgcttcttt attaccacga cctgatgaac    1680
cgaaaaggat cgatgtcatg aaacaactgt tcaaaaaatg actttcttca aacatctatg    1740
gcctcgttgg atctccgttg atgttgtggt ggttctgatg ctaaaacgac aaatagtgtt    1800
ataaccattg aagaagaaaa gaaaattaga gttgttgtat ctgcaaaaat tttggtagag    1860
acacgcaaac ccgtttggat tttgttatgg tgtaaagcgg ccgc                     1904
```

<210> SEQ ID NO 2
<211> LENGTH: 520
<212> TYPE: PRT
<213> ORGANISM: Arabidopsis thaliana

<400> SEQUENCE: 2

```
Met Ala Ile Leu Asp Ser Ala Gly Val Thr Thr Val Thr Glu Asn Gly
 1               5                  10                  15

Gly Gly Glu Phe Val Asp Leu Asp Arg Leu Arg Arg Arg Lys Ser Arg
             20                  25                  30

Ser Asp Ser Ser Asn Gly Leu Leu Leu Ser Gly Ser Asp Asn Asn Ser
         35                  40                  45

Pro Ser Asp Asp Val Gly Ala Pro Ala Asp Val Arg Asp Arg Ile Asp
     50                  55                  60

Ser Val Val Asn Asp Asp Ala Gln Gly Thr Ala Asn Leu Ala Gly Asp
 65                  70                  75                  80

Asn Asn Gly Gly Gly Asp Asn Asn Gly Gly Gly Arg Gly Gly Gly Glu
                 85                  90                  95

Gly Arg Gly Asn Ala Asp Ala Thr Phe Thr Tyr Arg Pro Ser Val Pro
            100                 105                 110

Ala His Arg Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Tyr Gly Trp
145                 150                 155                 160

Leu Ile Arg Thr Asp Phe Trp Phe Ser Ser Arg Ser Leu Arg Asp Trp
                165                 170                 175

Pro Leu Phe Met Cys Cys Ile Ser Leu Ser Ile Phe Pro Leu Ala Ala
            180                 185                 190

Phe Thr Val Glu Lys Leu Val Leu Gln Lys Tyr Ile Ser Glu Pro Val
        195                 200                 205

Val Ile Phe Leu His Ile Ile Ile Thr Met Thr Glu Val Leu Tyr Pro
    210                 215                 220

Val Tyr Val Thr Leu Arg Cys Asp Ser Ala Phe Leu Ser Gly Val Thr
225                 230                 235                 240

Leu Met Leu Leu Thr Cys Ile Val Trp Leu Lys Leu Val Ser Tyr Ala
                245                 250                 255
```

| | | | | | | | | | | | | |
|---|---|---|---|---|---|---|---|---|---|---|---|---|
|His|Thr|Ser|Tyr|Asp|Ile|Arg|Ser|Leu|Ala|Asn|Ala|Ala|Asp|Lys|Ala|
| | |260| | | |265| | | |270| | | | | |

Asn Pro Glu Val Ser Tyr Tyr Val Ser Leu Lys Ser Leu Ala Tyr Phe
            275                 280                 285

Met Val Ala Pro Thr Leu Cys Tyr Gln Pro Ser Tyr Pro Arg Ser Ala
            290                 295                 300

Cys Ile Arg Lys Gly Trp Val Ala Arg Gln Phe Ala Lys Leu Val Ile
305                 310                 315                 320

Phe Thr Gly Phe Met Gly Phe Ile Ile Glu Gln Tyr Ile Asn Pro Ile
                    325                 330                 335

Val Arg Asn Ser Lys His Pro Leu Lys Gly Asp Leu Leu Tyr Ala Ile
                340                 345                 350

Glu Arg Val Leu Lys Leu Ser Val Pro Asn Leu Tyr Val Trp Leu Cys
                355                 360                 365

Met Phe Tyr Cys Phe Phe His Leu Trp Leu Asn Ile Leu Ala Glu Leu
            370                 375                 380

Leu Cys Phe Gly Asp Arg Glu Phe Tyr Lys Asp Trp Asn Ala Lys
385                 390                 395                 400

Ser Val Gly Asp Tyr Trp Arg Met Trp Asn Met Pro Val His Lys Trp
                405                 410                 415

Met Val Arg His Ile Tyr Phe Pro Cys Leu Arg Ser Lys Ile Pro Lys
                420                 425                 430

Thr Leu Ala Ile Ile Ile Ala Phe Leu Val Ser Ala Val Phe His Glu
            435                 440                 445

Leu Cys Ile Ala Val Pro Cys Arg Leu Phe Lys Leu Trp Ala Phe Leu
450                 455                 460

Gly Ile Met Phe Gln Val Pro Leu Val Phe Ile Thr Asn Tyr Leu Gln
465                 470                 475                 480

Glu Arg Phe Gly Ser Thr Val Gly Asn Met Ile Phe Trp Phe Ile Phe
                485                 490                 495

Cys Ile Phe Gly Gln Pro Met Cys Val Leu Leu Tyr Tyr His Asp Leu
            500                 505                 510

Met Asn Arg Lys Gly Ser Met Ser
            515                 520

<210> SEQ ID NO 3
<211> LENGTH: 5193
<212> TYPE: DNA
<213> ORGANISM: Arabidopsis thaliana

<400> SEQUENCE: 3

```
gctcacgacc cattcttccc gttccatttg gtttttattta tttcaaagtt taatattcct    60
tttgtataac attcaaatct tcacatgatt gattgtgtga aaaccccaca gattttacta   120
caataggggg agttgactta aaatagctat tgatgtcgaa aaaatgtatt ttagtttataa   180 attatactaa agaaaatttt tgatttgtct gttgtttaag catatgtatt gttaaactta   240
aaaaaatatg tattgttaat cttaaaaatg taggagtaca catcaaatac tcgagcataa   300
tcaaaaccgt attcatagac cgatgtgaga atcaaataga agataatgtg attttttaaa   360
atatcgtatc tccaaatcaa tcacttagaa gataatgtaa ttctttatgt gctacataaa   420
taaatatata tatatatata tatatatatc ttgtatatat gtcttgacaa aaaattgcca   480
gtcaaaaacc atgactgaat caaactataa gtcggattga atcaaactat aagtcggatg   540
agtattaatt tccattatgt ttctatactt tacaaaccgg aaaatagata ttatagatac   600
```

```
caaaaaagta gatttgtgta tattattaga agatttggaa tttcatcatt atcaggatct     660
aaagtacttc cctaattaaa tcatgtcggt tgaaaaagct caatgaatgt tgaaatttg     720
gaaagtttat taaattcgga tcttttttt ttgtttgtcg tcccaaacat ttttatttta     780
ttacaaataa tcaacttatc cttactacta aatcatttca tatctttgat accaacaaat     840
catttccatat tctattttga tgtttaagaa aacactattt accagttaca aaatattata     900
aggattgttg tttagaaaaa aaagtacaag ttgaattctt tttgtcaaat ataaaattga     960
cttttttaata tataattgac ttattgaaca tgattacaga attaatcatc tacaaaactt    1020
tccaagtttta taataaatac atttcaaaga ctattagttc ttcttaaaat atttctaaaa    1080
gtgatcaaag actaccacat ataattcaga aaaagtagaa gttgatttct ttttgtcaaa    1140
taaataattg acttaaaata gtttggaaag ccattgaact tgattataga attgataatg    1200
tacataaaaa aattccaagt ttataataaa tacattttc  aaatgctata tcagttcttc    1260
ttaaaatatt tcactaaaaa aacactcaaa tatagaataa atttattgaa taacatacca    1320
actgtaaaac agaatttgac aaaaaaaaaa aaaaaatgaa atgaagatga agacaaaaat    1380
aaatcaccag aggatcttat gcaaaaaaat atatgaatac acaataaacc atattgatat    1440
ttttaaaata aaataaaaac agaaaaatat cccaacaccg cttttcaatt aaaaatcttc    1500
cgtcaccatt gttgtcatct tcctctctcg tgaatccttt ttcctttctt cttcttcttc    1560
tcttcagaga aaactttgct tctctttcta taaggaacca gacacgaatc ccattcccac    1620
cgatttctta gcttcttcct tcaatccgct cttttccctct ccattagatt ctgtttcctc    1680
tttcaatttc ttctgcatgc ttctcgattc tctctgacgc ctcttttctc ccgacgctgt    1740
ttcgtcaaac gcttttcgaa atggcgattt tggattctgc tggcgttact acggtgacgg    1800
agaacggtgg cggagagttc gtcgatcttg ataggcttcg tcgacggaaa tcgagatcgg    1860
attcttctaa cggacttctt ctctctggtt ccgataataa ttctccttcg gatgatgttg    1920
gagctcccgc cgacgttagg gatcggattg attccgttgt taacgatgac gctcagggaa    1980
cagccaattt ggccggagat aataacggtg gtggcgataa taacggtggt ggaagaggcg    2040
gcggagaagg aagaggaaac gccgatgcta cgtttacgta tcgaccgtcg gttccagctc    2100
atcggagggc gagagagagt ccacttagct ccgacgcaat cttcaaacag gtttaaaatc    2160
tcagaaatct tcgaatttgg tgtttgcttg ttgtttttata tggaattgag tttggtgatt    2220
gttttgcatt gcagagccat gccggattat tcaacctctg tgtagtagtt cttattgctg    2280
taaacagtag actcatcatc gaaaatctta tgaaggtttg ctgttacttg tttctccttt    2340
taggaattga attgcttgaa aatttatcag agacgaataa ctttgttgtt gctatcattc    2400
atgtagtatg gttggttgat cagaacggat ttctggttta gttcaagatc gctgcgagat    2460
tggccgcttt tcatgtgttg gtaaaagaag atgttttttta tttccagcaa tgttacattg    2520
ttatacgtat aatgatgagt ttagtgatca agttcctctt tgattcttct tcttgttgc     2580
agtatatccc tttcgatctt tccttttggct gcctttacgg ttgagaaatt ggtacttcag    2640
aaatacatat cagaacctgt gagtaattac tattctccag ccattactgt aatttttatt    2700
gaagacaagt tgtatcatg aagaacttac aagttctgtt tgaaaatgc tcaaggttgt      2760
catctttctt catattatta tcaccatgac agaggttttg tatccagttt acgtcaccct    2820
aaggtgatac tgttttctg gtctcagttt gtgatactgt ttttaagttt agttgtctga    2880
cccggtgatc ttgaaaatgg acaggtgtga ttctgctttt ttatcaggtg tcactttgat    2940
```

-continued

```
gctcctcact tgcattgtgt ggctaaagtt ggtttcttat gctcatacta gctatgacat      3000
aagatcccta gccaatgcag ctgataaggt aaaatacgaa aaagaagcgt atgtattagt      3060
cacttgcact gtgttactgt tttaaccaaa cactgttatg aactttaggc caatcctgaa      3120
gtctcctact acgttagctt gaagagcttg gcatatttca tggtcgctcc cacattgtgt      3180
tatcaggtaa ctgcaaagtg catcaaccat tcttatactt gcaagagttt cttgtctaaa      3240
cctcggatct ttgcttttcc ccagccaagt tatccacgtt ctgcatgtat acggaagggt      3300
tgggtggctc gtcaatttgc aaaactggtc atattcaccg gattcatggg atttataata      3360
gaacaagtac gttttcacat cttgctttat tagttttcct tggtgaaaat catcatccct      3420
gcgttgtcac cacttgactt catgttcttt tgttacattt tggcagtata taaatcctat      3480
tgtcaggaac tcaaagcatc ctttgaaagg cgatcttcta tatgctattg aaagagtgtt      3540
gaagctttca gttccaaatt tatatgtgtg gctctgcatg ttctactgct tcttccacct      3600
ttggtatgct gtgatcccat ctctttcaaa ataatttgca aattcgaaaa accgaaaaag      3660
gctaaatctc atacgaattt gatatttta gtttcttaga gtcggtgatg taatttcagt       3720
tactgaacgc aaatctcttg tccaaaggtt aaacatattg gcagagcttc tctgcttcgg      3780
ggatcgtgaa ttctacaaag attggtggaa tgcaaaaagt gtgggagatg tgagctattt      3840
tactcaaaag aaaacttatg atttttaatg ttgtcgttgt ttttgggtca tctaactaac      3900
caaattcatg tattcactgt cttcctttat cagtactgga gaatgtggaa tatggtatgg      3960
ttctcttcct aaacatcacc ttcttttgta cacaaaatag aagaagagag ctaattaaga      4020
tcttgttttc cttgacagcc tgttcataaa tggatggttc gacatatata cttcccgtgc      4080
ttgcgcagca agataccaaa ggtgagtgag atatataccg atatgcaatt gtcgagattt      4140
gtttctgtga tataaattta accctccaca cacttgtttt tcagacactc gccattatca      4200
ttgctttcct agtctctgca gtctttcatg aggtatacat actttctaca ttgccctgtc      4260
tctagacgca tgaacacacg ctagtgaaag aaatgctaat attcaaagca ttgttttac       4320
ttaacgatct tgtgttacaa atttcctttt gacagctatg catcgcagtt ccttgtcgtc      4380
tcttcaagct atgggctttt cttgggatta tgtttcaggt taaaaaatta ctaaactgct      4440
gcagtcgatt tttactaaac tctaatctca tattctgacc aaccaatttg tttgagtagg      4500
tgcctttggt cttcatcaca aactatctac aggaaaggtt tggctcaacg gtatgctctc      4560
aaaacccgag aaaatagaac gaataactct ttctttcata gcctagccat ttaaatcgca      4620
atgctgaaac ttaataataa aggtgatctg ttttggaatg ggatcatatt attaggtggg      4680
gaacatgatc ttctggttca tcttctgcat tttcggacaa ccgatgtgtg tgcttcttta      4740
ttaccacgac ctgatgaacc gaaaaggatc gatgtcatga acaactgtt caaaaaatga       4800
ctttcttcaa acatctatgg cctcgttgga tctccgttga tgttgtggtg gttctgatgc      4860
taaaacgaca aatagtgtta taaccattga agaagaaaag aaaattagag ttgttgtatc      4920
tgcaaaaatt ttggtagaga cacgcgaacc cgtttggatt tgttatggt gtaaagaaat        4980
ttcaatcaaa aaactgttgt aataattgtt accaaaaaga aatgcttttc tggaaacgag      5040
gggaaaaata gtagttttgt taggttttac tgtttggacc aaatctagta aaaaacttt       5100
tgtaataagg aaaaaaaaag aacaaatgtg ataaatgcat ggggattgta tgaaaccttc      5160
caataaagtt gattggtggt cccgtttttgg gga                                  5193
```

<210> SEQ ID NO 4
<211> LENGTH: 498

```
<212> TYPE: PRT
<213> ORGANISM: mouse

<400> SEQUENCE: 4
```

| | | | | | | | | | | | | | | | |
|---|---|---|---|---|---|---|---|---|---|---|---|---|---|---|---|
| Met | Gly | Asp | Arg | Gly | Gly | Ala | Gly | Ser | Ser | Arg | Arg | Arg | Thr | Gly | |
| 1 | | | | 5 | | | | | 10 | | | | | 15 | |
| Ser | Arg | Val | Ser | Val | Gln | Gly | Gly | Ser | Gly | Pro | Lys | Val | Glu | Glu | Asp |
| | | | 20 | | | | | 25 | | | | | 30 | | |
| Glu | Val | Arg | Asp | Ala | Ala | Val | Ser | Pro | Asp | Leu | Gly | Ala | Gly | Gly | Asp |
| | | | 35 | | | | | 40 | | | | | 45 | | |
| Ala | Pro | Ala | Pro | Ala | Pro | Ala | Pro | Ala | His | Thr | Arg | Asp | Lys | Asp | Gly |
| | | 50 | | | | | 55 | | | | | 60 | | | |
| Arg | Thr | Ser | Val | Gly | Asp | Gly | Tyr | Trp | Asp | Leu | Arg | Cys | His | Arg | Leu |
| 65 | | | | | 70 | | | | | 75 | | | | | 80 |
| Gln | Asp | Ser | Leu | Phe | Ser | Ser | Asp | Ser | Gly | Phe | Ser | Asn | Tyr | Arg | Gly |
| | | | | 85 | | | | | 90 | | | | | 95 | |
| Ile | Leu | Asn | Trp | Cys | Val | Val | Met | Leu | Ile | Leu | Ser | Asn | Ala | Arg | Leu |
| | | | 100 | | | | | 105 | | | | | 110 | | |
| Phe | Leu | Glu | Asn | Leu | Ile | Lys | Tyr | Gly | Ile | Leu | Val | Asp | Pro | Ile | Gln |
| | | 115 | | | | | 120 | | | | | 125 | | | |
| Val | Val | Ser | Leu | Phe | Leu | Lys | Asp | Pro | Tyr | Ser | Trp | Pro | Ala | Pro | Cys |
| | 130 | | | | | 135 | | | | | 140 | | | | |
| Val | Ile | Ile | Ala | Ser | Asn | Ile | Phe | Val | Val | Ala | Ala | Phe | Gln | Ile | Glu |
| 145 | | | | | 150 | | | | | 155 | | | | | 160 |
| Lys | Arg | Leu | Ala | Val | Gly | Ala | Leu | Thr | Glu | Gln | Met | Gly | Leu | Leu | Leu |
| | | | | 165 | | | | | 170 | | | | | 175 | |
| His | Val | Val | Asn | Leu | Ala | Thr | Ile | Ile | Cys | Phe | Pro | Ala | Ala | Val | Ala |
| | | | 180 | | | | | 185 | | | | | 190 | | |
| Leu | Leu | Val | Glu | Ser | Ile | Thr | Pro | Val | Gly | Ser | Val | Phe | Ala | Leu | Ala |
| | | 195 | | | | | 200 | | | | | 205 | | | |
| Ser | Tyr | Ser | Ile | Met | Phe | Leu | Lys | Leu | Tyr | Ser | Tyr | Arg | Asp | Val | Asn |
| | 210 | | | | | 215 | | | | | 220 | | | | |
| Leu | Trp | Cys | Arg | Gln | Arg | Arg | Val | Lys | Ala | Lys | Ala | Val | Ser | Thr | Gly |
| 225 | | | | | 230 | | | | | 235 | | | | | 240 |
| Lys | Lys | Val | Ser | Gly | Ala | Ala | Ala | Gln | Gln | Ala | Val | Ser | Tyr | Pro | Asp |
| | | | | 245 | | | | | 250 | | | | | 255 | |
| Asn | Leu | Thr | Tyr | Arg | Asp | Leu | Tyr | Tyr | Phe | Ile | Phe | Ala | Pro | Thr | Leu |
| | | | 260 | | | | | 265 | | | | | 270 | | |
| Cys | Tyr | Glu | Leu | Asn | Phe | Pro | Arg | Ser | Pro | Arg | Ile | Arg | Lys | Arg | Phe |
| | | 275 | | | | | 280 | | | | | 285 | | | |
| Leu | Leu | Arg | Arg | Val | Leu | Glu | Met | Leu | Phe | Phe | Thr | Gln | Leu | Gln | Val |
| | 290 | | | | | 295 | | | | | 300 | | | | |
| Gly | Leu | Ile | Gln | Gln | Trp | Met | Val | Pro | Thr | Ile | Gln | Asn | Ser | Met | Lys |
| 305 | | | | | 310 | | | | | 315 | | | | | 320 |
| Pro | Phe | Lys | Asp | Met | Asp | Tyr | Ser | Arg | Ile | Ile | Glu | Arg | Leu | Leu | Lys |
| | | | | 325 | | | | | 330 | | | | | 335 | |
| Leu | Ala | Val | Pro | Asn | His | Leu | Ile | Trp | Leu | Ile | Phe | Phe | Tyr | Trp | Phe |
| | | | 340 | | | | | 345 | | | | | 350 | | |
| Phe | His | Ser | Cys | Leu | Asn | Ala | Val | Ala | Glu | Leu | Leu | Gln | Phe | Gly | Asp |
| | | 355 | | | | | 360 | | | | | 365 | | | |
| Arg | Glu | Phe | Tyr | Arg | Asp | Trp | Trp | Asn | Ala | Glu | Ser | Val | Thr | Tyr | Phe |
| | 370 | | | | | 375 | | | | | 380 | | | | |
| Trp | Gln | Asn | Trp | Asn | Ile | Pro | Val | His | Lys | Trp | Cys | Ile | Arg | His | Phe |
| 385 | | | | | 390 | | | | | 395 | | | | | 400 |

```
Tyr Lys Pro Met Leu Arg His Gly Ser Ser Lys Trp Val Ala Arg Thr
                405                 410                 415
Gly Val Phe Leu Thr Ser Ala Phe His Glu Tyr Leu Val Ser Val
            420                 425                 430
Pro Leu Arg Met Phe Arg Leu Trp Ala Phe Thr Ala Met Met Ala Gln
            435                 440                 445
Val Pro Leu Ala Trp Ile Val Gly Arg Phe Phe Gln Gly Asn Tyr Gly
    450                 455                 460
Asn Ala Ala Val Trp Val Thr Leu Ile Ile Gly Gln Pro Val Ala Val
465                 470                 475                 480
Leu Met Tyr Val His Asp Tyr Tyr Val Leu Asn Tyr Asp Ala Pro Val
                485                 490                 495
Gly Val

<210> SEQ ID NO 5
<211> LENGTH: 488
<212> TYPE: PRT
<213> ORGANISM: human

<400> SEQUENCE: 5

Met Gly Asp Arg Gly Ser Ser Arg Arg Arg Thr Gly Ser Arg Pro
 1               5                  10                  15
Ser Ser His Gly Gly Gly Pro Ala Ala Glu Glu Val Arg
            20                  25                  30
Asp Ala Ala Ala Gly Pro Asp Val Gly Ala Ala Gly Asp Ala Pro Ala
            35                  40                  45
Pro Ala Pro Asn Lys Asp Gly Asp Ala Gly Val Gly Ser Gly His Trp
    50                  55                  60
Glu Leu Arg Cys His Arg Leu Gln Asp Ser Leu Phe Ser Ser Asp Ser
65                  70                  75                  80
Gly Phe Ser Asn Tyr Arg Gly Ile Leu Asn Trp Cys Val Val Met Leu
                85                  90                  95
Ile Leu Ser Asn Ala Arg Leu Phe Leu Glu Asn Leu Ile Lys Tyr Gly
            100                 105                 110
Ile Leu Val Asp Pro Ile Gln Val Val Ser Leu Phe Leu Lys Asp Pro
            115                 120                 125
His Ser Trp Pro Ala Pro Cys Leu Val Ile Ala Ala Asn Val Phe Ala
    130                 135                 140
Val Ala Ala Phe Gln Val Glu Lys Arg Leu Ala Val Gly Ala Leu Thr
145                 150                 155                 160
Glu Gln Ala Gly Leu Leu Leu His Val Ala Asn Leu Ala Thr Ile Leu
                165                 170                 175
Cys Phe Pro Ala Ala Val Val Leu Leu Val Glu Ser Ile Thr Pro Val
            180                 185                 190
Gly Ser Leu Leu Ala Leu Met Ala His Thr Ile Leu Phe Leu Lys Leu
            195                 200                 205
Phe Ser Tyr Arg Asp Val Asn Ser Trp Cys Arg Arg Ala Arg Ala Lys
    210                 215                 220
Ala Ala Ser Ala Gly Lys Lys Ala Ser Ser Ala Ala Pro His Thr
225                 230                 235                 240
Val Ser Tyr Pro Asp Asn Leu Thr Tyr Arg Asp Leu Tyr Tyr Phe Leu
                245                 250                 255
Phe Ala Pro Thr Leu Cys Tyr Glu Leu Asn Phe Pro Arg Ser Pro Arg
            260                 265                 270
```

```
Ile Arg Lys Arg Phe Leu Leu Arg Arg Ile Leu Glu Met Leu Phe Phe
        275                 280                 285

Thr Gln Leu Gln Val Gly Leu Ile Gln Gln Trp Met Val Pro Thr Ile
        290                 295                 300

Gln Asn Ser Met Lys Pro Phe Lys Asp Met Asp Tyr Ser Arg Ile Ile
305                 310                 315                 320

Glu Arg Leu Leu Lys Leu Ala Val Pro Asn His Leu Ile Trp Leu Ile
                325                 330                 335

Phe Phe Tyr Trp Leu Phe His Ser Cys Leu Asn Ala Val Ala Glu Leu
            340                 345                 350

Met Gln Phe Gly Asp Arg Glu Phe Tyr Arg Asp Trp Asn Ser Glu
        355                 360                 365

Ser Val Thr Tyr Phe Trp Gln Asn Trp Asn Ile Pro Val His Lys Trp
    370                 375                 380

Cys Ile Arg His Phe Tyr Lys Pro Met Leu Arg Arg Gly Ser Ser Lys
385                 390                 395                 400

Trp Met Ala Arg Thr Gly Val Phe Leu Ala Ser Ala Phe Phe His Glu
                405                 410                 415

Tyr Leu Val Ser Val Pro Leu Arg Met Phe Arg Leu Trp Ala Phe Thr
            420                 425                 430

Gly Met Met Ala Gln Ile Pro Leu Ala Trp Phe Val Gly Arg Phe Phe
        435                 440                 445

Gln Gly Asn Tyr Gly Asn Ala Ala Val Trp Leu Ser Leu Ile Ile Gly
    450                 455                 460

Gln Pro Ile Ala Val Leu Met Tyr Val His Asp Tyr Val Leu Asn
465                 470                 475                 480

Tyr Glu Ala Pro Ala Ala Glu Ala
                485

<210> SEQ ID NO 6
<211> LENGTH: 629
<212> TYPE: DNA
<213> ORGANISM: Arabidopsis thaliana
<220> FEATURE:
<221> NAME/KEY: misc_feature
<222> LOCATION: (455)..(455)
<223> OTHER INFORMATION: the 'n' at position 455 may be any nucleic acid
<220> FEATURE:
<221> NAME/KEY: misc_feature
<222> LOCATION: (464)..(464)
<223> OTHER INFORMATION: the 'n' at position 464 may be any nucleic acid
<220> FEATURE:
<221> NAME/KEY: misc_feature
<222> LOCATION: (467)..(467)
<223> OTHER INFORMATION: the 'n' at position 467 may be any nucleic acid
<220> FEATURE:
<221> NAME/KEY: misc_feature
<222> LOCATION: (475)..(475)
<223> OTHER INFORMATION: the 'n' at position 475 may be any nucleic acid
<220> FEATURE:
<221> NAME/KEY: misc_feature
<222> LOCATION: (497)..(497)
<223> OTHER INFORMATION: the 'n' at position 497 may be any nucleic acid
<220> FEATURE:
<221> NAME/KEY: misc_feature
<222> LOCATION: (500)..(500)
<223> OTHER INFORMATION: the 'n' at position 500 may be any nucleic acid
<220> FEATURE:
<221> NAME/KEY: misc_feature
<222> LOCATION: (508)..(508)
<223> OTHER INFORMATION: the 'n' at position 508 may be any nucleic acid
<220> FEATURE:
<221> NAME/KEY: misc_feature
<222> LOCATION: (514)..(514)
```

```
<223> OTHER INFORMATION: the 'n' at position 514 may be any nucleic acid
<220> FEATURE:
<221> NAME/KEY: misc_feature
<222> LOCATION: (519)..(519)
<223> OTHER INFORMATION: the 'n' at position 519 may be any nucleic acid
<220> FEATURE:
<221> NAME/KEY: misc_feature
<222> LOCATION: (536)..(436)
<223> OTHER INFORMATION: the 'n' at position 536 may be any nucleic acid
<220> FEATURE:
<221> NAME/KEY: misc_feature
<222> LOCATION: (543)..(544)
<223> OTHER INFORMATION: the 'n' at positions 543 and 544 may be any
      nucleic acid
<220> FEATURE:
<221> NAME/KEY: misc_feature
<222> LOCATION: (576)..(576)
<223> OTHER INFORMATION: the 'n' at position 576 may be any nucleic acid
<220> FEATURE:
<221> NAME/KEY: misc_feature
<222> LOCATION: (583)..(584)
<223> OTHER INFORMATION: the 'n' at positions 583 and 584 may be any
      nucleic acid
<220> FEATURE:
<221> NAME/KEY: misc_feature
<222> LOCATION: (597)..(597)
<223> OTHER INFORMATION: the 'n' at position 597 may be any nucleic acid

<400> SEQUENCE: 6
tgcatgtata cggaagggtt gggtggctcg tcaatttgca aaactggtca tattcaccgg     60
attcatggga tttataatag aacaatatat aaatcctatt gtcaggaact caaagcatcc    120
tttgaaaggc gatcttctat atgctattga agagtgttg aagctttcag ttccaaattt     180
atatgtgtgg ctctgcatgt tctactgctt cttccacctt tggttaaaca tattggcaga    240
gcttctctgc ttcggggatc gtgaattcta caaagattgg tggaatgcaa aaagtgtggg    300
agattactgg gagaatgtgg aatatgcctg tccataaatg ggatgggtcc gacatatata    360
ccttccccgt gcttgcgcac aaggattacc caaagacacc ccggccatta accattggct    420
ttcccaagcc ccctggaggc ctttccatgg gccanggacc cggngtnccc tggcnggccc    480
ttcaaagcaa aggggnttn cctggggnta aagntccang ggccccttggg gcccanccaa    540 aanttcccc cgggaaaggg ttgcccaccg ggggngaaa aanncccggg ggcaccncgg     600
aattttggga acccggggg ggccttttt                                       629

<210> SEQ ID NO 7
<211> LENGTH: 11
<212> TYPE: PRT
<213> ORGANISM: Arabidopsis thaliana

<400> SEQUENCE: 7

His Lys Trp Met Val Arg His Ile Tyr Phe Pro
1               5                   10

<210> SEQ ID NO 8
<211> LENGTH: 341
<212> TYPE: PRT
<213> ORGANISM: Brassica napus

<400> SEQUENCE: 8

Met Cys Cys Leu Ser Leu Ser Ile Phe Pro Leu Ala Ala Phe Thr Val
1               5                   10                  15

Glu Lys Leu Val Leu Gln Lys Cys Ile Ser Glu Pro Val Val Ile Phe
            20                  25                  30

Leu His Val Ile Ile Thr Met Thr Glu Val Leu Tyr Pro Val Tyr Val
        35                  40                  45
```

```
Thr Leu Arg Cys Asp Ser Ala Phe Leu Ser Gly Asp Thr Leu Met Leu
         50                  55                  60

Leu Thr Cys Ile Val Trp Leu Lys Leu Val Ser Tyr Ala His Thr Asn
 65                  70                  75                  80

Tyr Asp Ile Arg Thr Leu Ala Asn Ser Ser Asp Lys Ala Asn Pro Glu
                 85                  90                  95

Val Ser Tyr Tyr Val Ser Leu Lys Ser Leu Ala Tyr Phe Met Leu Ala
            100                 105                 110

Pro Thr Leu Cys Tyr Gln Pro Ser Tyr Pro Arg Ser Pro Cys Ile Arg
            115                 120                 125

Lys Gly Trp Val Ala Arg Gln Phe Ala Lys Leu Val Ile Phe Thr Gly
130                 135                 140

Leu Met Gly Phe Ile Ile Glu Gln Tyr Ile Asn Pro Ile Val Arg Asn
145                 150                 155                 160

Ser Lys His Pro Leu Lys Gly Asp Leu Leu Tyr Ala Ile Glu Arg Val
                165                 170                 175

Leu Lys Leu Ser Val Pro Asn Leu Tyr Val Trp Leu Cys Met Phe Tyr
            180                 185                 190

Cys Phe Phe His Leu Trp Leu Asn Ile Leu Ala Glu Leu Leu Cys Phe
            195                 200                 205

Gly Asp Arg Glu Phe Tyr Lys Asp Trp Trp Asn Ala Lys Ser Val Gly
210                 215                 220

Asp Tyr Trp Arg Met Trp Asn Met Pro Val His Lys Trp Met Val Arg
225                 230                 235                 240

His Val Tyr Phe Pro Cys Leu Arg Ile Lys Ile Pro Lys Val Pro Ala
                245                 250                 255

Ile Ile Ile Ala Phe Leu Val Ser Ala Val Phe His Glu Leu Cys Ile
            260                 265                 270

Ala Val Pro Cys Arg Leu Phe Asn Leu Trp Ala Phe Met Gly Ile Met
            275                 280                 285

Phe Gln Val Pro Leu Val Phe Ile Thr Asn Phe Leu Gln Glu Arg Phe
290                 295                 300

Gly Ser Met Val Gly Asn Met Ile Phe Gly Ser Ala Ser Cys Ile Phe
305                 310                 315                 320

Gly Gln Pro Met Cys Gly Leu Leu Tyr Tyr His Asp Leu Met Asn Arg
                325                 330                 335

Lys Gly Ser Met Ser
            340

<210> SEQ ID NO 9
<211> LENGTH: 503
<212> TYPE: PRT
<213> ORGANISM: Brassica napus

<400> SEQUENCE: 9

Met Ala Ile Leu Asp Ser Gly Gly Val Ala Val Pro Pro Thr Glu Asn
 1               5                  10                  15

Gly Val Ala Asp Leu Asp Arg Leu His Arg Arg Lys Ser Ser Ser Asp
            20                  25                  30

Ser Ser Asn Gly Leu Leu Ser Asp Thr Ser Pro Ser Asp Asp Val Gly
        35                  40                  45

Ala Ala Ala Ala Glu Arg Asp Arg Val Asp Ser Ala Ala Glu Glu Glu
    50                  55                  60

Ala Gln Gly Thr Ala Asn Leu Ala Gly Gly Asp Ala Glu Thr Arg Glu
```

-continued

```
                65                  70                  75                  80
Ser Ala Gly Gly Asp Val Arg Phe Thr Tyr Arg Pro Ser Val Pro Ala
                    85                  90                  95
His Arg Arg Thr Arg Glu Ser Pro Leu Ser Ser Asp Ala Ile Phe Lys
                    100                 105                 110
Gln Ser His Ala Gly Leu Phe Asn Leu Cys Val Val Leu Val Ala
                    115                 120                 125
Val Asn Ser Arg Leu Ile Ile Glu Asn Leu Met Lys Tyr Gly Trp Leu
        130                 135                 140
Ile Arg Thr Asp Phe Trp Phe Ser Ser Thr Ser Leu Arg Asp Trp Pro
145                 150                 155                 160
Leu Phe Met Cys Cys Leu Ser Leu Ser Val Phe Pro Leu Ala Ala Phe
                    165                 170                 175
Thr Val Glu Lys Met Val Leu Gln Lys Phe Ile Ser Glu Pro Val Ala
                    180                 185                 190
Ile Ile Leu His Val Ile Ile Thr Met Thr Glu Val Leu Tyr Pro Val
                    195                 200                 205
Tyr Val Thr Leu Arg Cys Asp Ser Ala Phe Leu Ser Gly Val Thr Leu
        210                 215                 220
Met Leu Leu Thr Cys Ile Val Trp Leu Lys Leu Val Ser Tyr Ala His
225                 230                 235                 240
Thr Ser Tyr Asp Ile Arg Thr Leu Ala Asn Ser Ala Asp Lys Val Asp
                    245                 250                 255
Pro Glu Ile Ser Tyr Tyr Val Ser Leu Lys Ser Leu Ala Tyr Phe Met
                    260                 265                 270
Val Ala Pro Thr Leu Cys Tyr Gln Pro Ser Tyr Pro Arg Ser Pro Cys
                    275                 280                 285
Ile Arg Lys Gly Trp Val Ala Arg Gln Leu Ala Lys Leu Val Ile Phe
        290                 295                 300
Thr Gly Leu Met Gly Phe Ile Ile Glu Gln Tyr Ile Asn Pro Ile Val
305                 310                 315                 320
Arg Asn Ser Lys His Pro Leu Lys Gly Asp Leu Leu Tyr Ala Ile Glu
                    325                 330                 335
Arg Val Leu Lys Leu Ser Val Pro Asn Leu Tyr Val Trp Leu Cys Met
                    340                 345                 350
Phe Tyr Cys Phe Phe His Leu Trp Leu Asn Ile Leu Ala Glu Leu Leu
                    355                 360                 365
Cys Phe Gly Asp Arg Glu Phe Tyr Lys Asp Trp Asn Ala Lys Ser
        370                 375                 380
Val Gly Asp Tyr Trp Arg Met Trp Asn Met Pro Val His Lys Trp Met
385                 390                 395                 400
Val Arg His Val Tyr Phe Pro Cys Leu Arg Ile Lys Ile Pro Lys Val
                    405                 410                 415
Pro Ala Ile Ile Ile Ala Phe Leu Val Ser Ala Val Phe His Glu Leu
                    420                 425                 430
Cys Ile Ala Val Pro Cys Arg Leu Phe Asn Leu Trp Ala Phe Met Gly
                    435                 440                 445
Ile Met Phe Gln Val Pro Leu Val Phe Ile Thr Asn Phe Leu Gln Glu
        450                 455                 460
Arg Phe Gly Ser Met Val Gly Asn Met Ile Phe Gly Ser Ala Ser Cys
465                 470                 475                 480
Ile Phe Gly Gln Pro Met Cys Gly Leu Leu Tyr Tyr His Asp Leu Met
                    485                 490                 495
```

-continued

Asn Arg Lys Gly Ser Met Ser
            500

<210> SEQ ID NO 10
<211> LENGTH: 11
<212> TYPE: PRT
<213> ORGANISM: Arabidopsis thaliana
<220> FEATURE:
<221> NAME/KEY: misc_feature
<222> LOCATION: (1)..(1)
<223> OTHER INFORMATION: the Xaa at position 1 may be any amino acid
<220> FEATURE:
<221> NAME/KEY: misc_feature
<222> LOCATION: (3)..(3)
<223> OTHER INFORMATION: the Xaa at position 3 may be any amino acid
<220> FEATURE:
<221> NAME/KEY: misc_feature
<222> LOCATION: (5)..(6)
<223> OTHER INFORMATION: the Xaa at positions 5 and 6 may be any amino
      acid
<220> FEATURE:
<221> NAME/KEY: misc_feature
<222> LOCATION: (8)..(10)
<223> OTHER INFORMATION: the Xaa at positions 8 through 10 may be any
      amino acid

<400> SEQUENCE: 10

Xaa Leu Xaa Lys Xaa Xaa Ser Xaa Xaa Xaa Val
  1               5                  10

<210> SEQ ID NO 11
<211> LENGTH: 27
<212> TYPE: PRT
<213> ORGANISM: Arabidopsis thaliana

<400> SEQUENCE: 11

Ser His Ala Gly Leu Phe Asn Leu Cys Val Val Leu Ile Ala Val
  1               5                  10                  15

Asn Ser Arg Leu Ile Ile Glu Asn Leu Met Lys
            20                  25

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer of
      DGATXba1

<400> SEQUENCE: 12
ctagtctaga atggcgattt tgga                                          24

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence: Primer of
      DGATXho1

<400> SEQUENCE: 13
gcgctcgagt ttcatgacat cga                                           23

<210> SEQ ID NO 14
<211> LENGTH: 24
<212> TYPE: DNA
<213> ORGANISM: Artificial Sequence
<220> FEATURE:

```
<223> OTHER INFORMATION: Description of Artificial Sequence: Primer
      DGAT1

<400> SEQUENCE: 14
agacacgaat cccattccca ccga                                          24

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence: Primer
      DGAT2

<400> SEQUENCE: 15
agtggtgaca acgcagggat gatg                                          24

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Primer
      DGAT3

<400> SEQUENCE: 16
atggtcgctc ccacattgtg t                                             21

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence: Primer
      DGAT4

<400> SEQUENCE: 17
catacaatcc ccatgacatt tatca                                         25

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Primer A

<400> SEQUENCE: 18
cgaccgtcgg ttccagctca tcgg                                          24

<210> SEQ ID NO 19
<211> LENGTH: 24
<212> TYPE: DNA
<213> ORGANISM: Artificial Sequence
<220> FEATURE:
<223> OTHER INFORMATION: Description of Artificial Sequence: Primer B

<400> SEQUENCE: 19
gcggccaatc tcgcagcgat cttg                                          24

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Primer C

<400> SEQUENCE: 20
```

```
taaacagtag actcatcatc g                                              21

<210> SEQ ID NO 21
<211> LENGTH: 33
<212> TYPE: DNA
<213> ORGANISM: Artificial Sequence
<220> FEATURE:
<223> OTHER INFORMATION: Description of Artificial Sequence: Primer Gen
      1

<400> SEQUENCE: 21
gagaggatcc acgctcacga cccattcttc ccg                                 33

<210> SEQ ID NO 22
<211> LENGTH: 33
<212> TYPE: DNA
<213> ORGANISM: Artificial Sequence
<220> FEATURE:
<223> OTHER INFORMATION: Description of Artificial Sequence: Primer Gen
      2

<400> SEQUENCE: 22
aagaaggatc catccccaaa acgggaccac caa                                 33

<210> SEQ ID NO 23
<211> LENGTH: 1985
<212> TYPE: DNA
<213> ORGANISM: Arabidopsis thaliana

<400> SEQUENCE: 23
atttcttagc ttcttccttc aatccgctct ttccctctcc attagattct gtttcctctt    60
tcaatttctt ctgcatgctt ctcgattctc tctgacgcct cttttctccc gacgctgttt   120
cgtcaaacgc ttttcgaaat ggcgattttg gattctgctg gcgttactac ggtgacggag   180
aacggtggcg gagagttcgt cgatcttgat aggcttcgtc gacggaaatc gagatcggat   240
tcttctaacg gacttcttct ctctggttcc gataataatt ctccttcgga tgatgttgga   300
gctcccgccg acgttaggga tcggattgat tccgttgtta acgatgacgc tcagggaaca   360
gccaatttgg ccggagataa taacggtggt ggcgataata acggtggtgg aagaggcggc   420
ggagaaggaa gaggaaacgc cgatgctacg tttacgtatc gaccgtcggt tccagctcat   480
cggagggcga gagagagtcc acttagctcc gacgcaatct tcaaacagag ccatgccgga   540
ttattcaacc tctgtgtagt agttcttatt gctgtaaaca gtagactcat catcgaaaat   600
cttatgaaga gccatgccgg attattcaac ctctgtgtag tagttcttat tgctgtaaac   660
agtagactca tcatcgaaaa tcttatgaag tatggttggt tgatcagaac ggatttctgg   720
tttagttcaa gatcgctgcg agattggccg cttttcatgt gttgtatatc cctttcgatc   780
tttcctttgg ctgcctttac ggttgagaaa ttggtacttc agaaatacat atcagaacct   840
gttgtcatct ttcttcatat tattatcacc atgacagagg ttttgtatcc agtttacgtc   900
accctaaggt gtgattctgc tttttttatca ggtgtcactt tgatgctcct cacttgcatt   960
gtgtggctaa agttggtttc ttatgctcat actagctatg acataagatc cctagccaat  1020
gcagctgata aggccaatcc tgaagtctcc tactacgtta gcttgaagag cttggcatat  1080
ttcatggtcg ctcccacatt gtgttatcag ccaagttatc cacgttctgc atgtatacgg  1140
aagggttggg tggctcgtca atttgcaaaa ctggtcatat tcaccggatt catgggattt  1200
ataatagaac aatatataaa tcctattgtc aggaactcaa agcatccttt gaaaggcgat  1260
```

```
cttctatatg ctattgaaag agtgttgaag ctttcagttc caaatttata tgtgtggctc   1320
tgcatgttct actgcttctt ccacctttgg ttaaacatat tggcagagct tctctgcttc   1380
ggggatcgtg aattctacaa agattggtgg aatgcaaaaa gtgtgggaga ttactggaga   1440
atgtggaata tgcctgttca taaatggatg gttcgacata tatacttccc gtgcttgcgc   1500
agcaagatac caaagacact cgccattatc attgctttcc tagtctctgc agtctttcat   1560
gagctatgca tcgcagttcc ttgtcgtctc ttcaagctat gggcttttct tgggattatg   1620
tttcaggtgc ctttggtctt catcacaaac tatctacagg aaaggtttgg ctcaacggtg   1680
gggaacatga tcttctggtt catcttctgc attttcggac aaccgatgtg tgtgcttctt   1740
tattaccacg acctgatgaa ccgaaaagga tcgatgtcat gaaacaactg ttcaaaaaat   1800
gactttcttc aaacatctat ggcctcgttg atctccgtt gatgttgtgg tggttctgat   1860
gctaaaacga caaatagtgt tataaccatt gaagaagaaa agaaaattag agttgttgta   1920
tctgcaaaaa ttttggtaga gacacgcaaa cccgtttgga ttttgttatg gtgtaaagcg   1980
gccgc                                                               1985

<210> SEQ ID NO 24
<211> LENGTH: 5339
<212> TYPE: DNA
<213> ORGANISM: Arabidopsis thaliana

<400> SEQUENCE: 24
gctcacgacc cattcttccc gttccatttg gttttattta tttcaaagtt taatattcct     60
tttgtataac attcaaatct tcacatgatt gattgtgtga aaccccaca gattttacta    120 caatagggggg agttgactta aaatagctat tgatgtcgaa aaaatgtatt ttagttataa    180
attatactaa agaaaatttt tgatttgtct gttgtttaag catatgtatt gttaaactta    240
aaaaaatatg tattgttaat cttaaaaatg taggagtaca catcaaatac tcgagcataa    300
tcaaaaccgt attcatagac cgatgtgaga atcaaataga agataatgtg attttttaaa    360
atatcgtatc tccaaatcaa tcacttagaa gataatgtaa ttctttatgt gctacataaa    420
taaatatata tatatatata tatatatatc ttgtatatat gtcttgacaa aaaattgcca    480
gtcaaaaacc atgactgaat caaactataa gtcggattga atcaaactat aagtcggatg    540
agtattaatt tccattatgt ttctatactt tacaaaccgg aaaatagata ttatagatac    600 caaaaagta gatttgtgta tattattaga agatttggaa tttcatcatt atcaggatct    660
aaagtacttc cctaattaaa tcatgtcggt tgaaaaagct caatgaatgt ttgaaatttg    720
gaaagtttat taaattcgga tcttttttttt ttgtttgtcg tcccaaacat ttttattta    780 ttacaaataa tcaacttatc cttactacta aatcattca tatctttgat accaacaaat    840
catttcatat tctatttga tgtttaagaa aacactattt accagttaca aaatattata    900
aggattgttg tttagaaaaa aaagtacaag ttgaattctt tttgtcaaat ataaaattga    960 cttttttaata tataattgac ttattgaaca tgattacaga attaatcatc tacaaaactt   1020
tccaagttta taataaatac atttcaaaga ctattagttc ttcttaaaat atttctaaaa   1080
gtgatcaaag actaccacat ataattcaga aaagtagaa gttgatttct ttttgtcaaa   1140
taaataattg acttaaaata gtttggaaag ccattgaact tgattataga attgataatg   1200
tacataaaaa aattccaagt ttataataaa tacattttc aaatgctata tcagttcttc   1260 ttaaatatt tcactaaaaa aacactcaaa tatagaataa atttattgaa taacatacca   1320
actgtaaaac agaatttgac aaaaaaaaaaa aaaaaatgaa atgaagatga agacaaaat   1380
```

```
aaatcaccag aggatcttat gcaaaaaaat atatgaatac acaataaacc atattgatat    1440
ttttaaaata aaataaaaac agaaaaatat cccaacaccg cttttcaatt aaaaatcttc    1500
cgtcaccatt gttgtcatct tcctctctcg tgaatccttt ttccttctt cttcttcttc     1560 tcttcagaga aaactttgct tctctttcta taaggaacca gacacgaatc ccattcccac    1620
cgatttctta gcttcttcct tcaatccgct cttccctct ccattagatt ctgtttcctc    1680
tttcaatttc ttctgcatgc ttctcgattc tctctgacgc ctctttctc ccgacgctgt    1740 ttcgtcaaac gcttttcgaa atggcgattt tggattctgc tggcgttact acggtgacgg    1800
agaacggtgg cggagagttc gtcgatcttg ataggcttcg tcgacggaaa tcgagatcgg    1860
attcttctaa cggacttctt ctctctggtt ccgataataa ttctccttcg gatgatgttg    1920
gagctcccgc cgacgttagg gatcggattg attccgttgt taacgatgac gctcagggaa    1980
cagccaattt ggccggagat aataacggtg gtggcgataa taacggtggt ggaagaggcg    2040
gcggagaagg aagaggaaac gccgatgcta cgtttacgta tcgaccgtcg gttccagctc    2100
atcggagggc gagagagagt ccacttagct ccgacgcaat cttcaaacag gtttaaaatc    2160
tcagaaatct tcgaatttgg tgtttgcttg ttgttttata tggaattgag tttggtgatt    2220
gttttgcatt gcagagccat gccggattat tcaacctctg tgtagtagtt cttattgctg    2280
taaacagtag actcatcatc gaaaatctta tgaaggtttg ctgttacttg tttctccttt    2340
taggaattga attgcttgaa aatttatcat tgcattgcag agccatgccg gattattcaa    2400
cctctgtgta gtagttctta ttgctgtaaa cagtagactc atcatcgaaa atcttatgaa    2460
ggtttgctgt tacttgtttc tccttttagg aattgaattg cttgaaaatt tatcagagac    2520
gaataacttt gttgttgcta tcattcatgt agtatggttg gttgatcaga acggatttct    2580
ggtttagttc aagatcgctg cgagattggc cgcttttcat gtgttggtaa agaagatgt     2640 tttttatttc cagcaatgtt acattgttat acgtataatg atgagtttag tgatcaagtt    2700
cctctttgat tcttctttct tgttgcagta tatcccttc gatctttcct ttggctgcct     2760
ttacggttga gaaattggta cttcagaaat acatatcaga acctgtgagt aattactatt    2820
ctccagccat tactgtaatt tttattgaag acaagtttgt atcatgaaga acttacaagt    2880
tctgttttga aaatgctcaa ggttgtcatc tttcttcata ttattatcac catgacagag    2940
gttttgtatc cagtttacgt caccctaagg tgatactgtt tttctggtct cagtttgtga    3000
tactgttttt aagtttagtt gtctgacccg tgatcttga aaatggacag gtgtgattct     3060
gcttttttat caggtgtcac tttgatgctc ctcacttgca ttgtgtggct aaagttggtt    3120
tcttatgctc atactagcta tgacataaga tccctagcca atgcagctga taaggtaaaa    3180
tacgaaaaag aagcgtatgt attagtcact tgcactgtgt tactgttta accaaacact     3240 gttatgaact ttaggccaat cctgaagtct cctactacgt tagcttgaag agcttggcat    3300
atttcatggt cgctcccaca ttgtgttatc aggtaactgc aaagtgcatc aaccattctt    3360
atacttgcaa gagtttcttg tctaaacctc ggatctttgc ttttccccag ccaagttatc    3420
cacgttctgc atgtatacgg aagggttggg tggctcgtca atttgcaaaa ctggtcatat    3480
tcaccggatt catgggattt ataatagaac aagtacgttt tcacatcttg ctttattagt    3540
tttccttggt gaaaatcatc atccctgcgt tgtcaccact tgacttcatg ttcttttgtt    3600 acatttggc agtatataaa tcctattgtc aggaactcaa agcatccttt gaaaggcgat     3660
cttctatatg ctattgaaag agtgttgaag ctttcagttc caaatttata tgtgtggctc    3720
```

```
tgcatgttct actgcttctt ccacctttgg tatgctgtga tcccatctct ttcaaaataa    3780
tttgcaaatt cgaaaaaccg aaaaaggcta atctcatac gaatttgata ttttagttt      3840
cttagagtcg gtgatgtaat ttcagttact gaacgcaaat ctcttgtcca aaggttaaac    3900
atattggcag agcttctctg cttcggggat cgtgaattct acaaagattg gtggaatgca    3960
aaaagtgtgg gagatgtgag ctattttact caaaagaaaa cttatgattt ttaatgttgt    4020
cgttgttttt gggtcatcta actaaccaaa ttcatgtatt cactgtcttc ctttatcagt    4080
actggagaat gtggaatatg gtatggttct cttcctaaac atcaccttct tttgtacaca    4140
aaatagaaga agagagctaa ttaagatctt gttttccttg acagcctgtt cataaatgga    4200
tggttcgaca tatatacttc ccgtgcttgc gcagcaagat accaaaggtg agtgagatat    4260
ataccgatat gcaattgtcg agatttgttt ctgtgatata aatttaaccc tccacacact    4320
tgtttttcag acactcgcca ttatcattgc tttcctagtc tctgcagtct ttcatgaggt    4380
atacatactt tctacattgc cctgtctcta gacgcatgaa cacacgctag tgaaagaaat    4440
gctaatattc aaagcattgt ttttacttaa cgatcttgtg ttacaaattt ccttttgaca    4500
gctatgcatc gcagttcctt gtcgtctctt caagctatgg gcttttcttg ggattatgtt    4560
tcaggttaaa aaattactaa actgctgcag tcgatttta ctaaactcta atctcatatt     4620
ctgaccaacc aatttgtttg agtaggtgcc tttggtcttc atcacaaact atctacagga    4680
aaggtttggc tcaacggtat gctctcaaaa cccgagaaaa tagaacgaat aactctttct    4740
ttcatagcct agccatttaa atcgcaatgc tgaaacttaa taataaaggt gatctgtttt    4800
ggaatgggat catattatta ggtggggaac atgatcttct ggttcatctt ctgcattttc    4860
ggacaaccga tgtgtgtgct tctttattac cacgacctga tgaaccgaaa aggatcgatg    4920
tcatgaaaca actgttcaaa aaatgacttt cttcaaacat ctatggcctc gttggatctc    4980
cgttgatgtt gtggtggttc tgatgctaaa acgacaaata gtgttataac cattgaagaa    5040
gaaaagaaaa ttagagttgt tgtatctgca aaaatttggt agagacacg cgaacccgtt     5100
tggattttgt tatggtgtaa agaaatttca atcaaaaaac tgttgtaata attgttacca    5160
aaaagaaatg cttttctgga aacgagggga aaaatagtag ttttgttagg ttttactgtt    5220
tggaccaaat ctagtaaaaa actttttgta ataaggaaaa aaaagaaca aatgtgataa     5280
atgcatgggg attgtatgaa accttccaat aaagttgatt ggtggtcccg ttttggggga    5339
```

<210> SEQ ID NO 25
<211> LENGTH: 547
<212> TYPE: PRT
<213> ORGANISM: Arabidopsis thaliana

<400> SEQUENCE: 25

Met Ala Ile Leu Asp Ser Ala Gly Val Thr Thr Val Thr Glu Asn Gly
1               5                   10                  15

Gly Gly Glu Phe Val Asp Leu Asp Arg Leu Arg Arg Lys Ser Arg
        20                  25                  30

Ser Asp Ser Ser Asn Gly Leu Leu Leu Ser Gly Ser Asp Asn Asn Ser
    35                  40                  45

Pro Ser Asp Asp Val Gly Ala Pro Ala Asp Val Arg Asp Arg Ile Asp
    50                  55                  60

Ser Val Val Asn Asp Asp Ala Gln Gly Thr Ala Asn Leu Ala Gly Asp
65                  70                  75                  80

Asn Asn Gly Gly Gly Asp Asn Asn Gly Gly Gly Arg Gly Gly Gly Glu
                85                  90                  95

```
Gly Arg Gly Asn Ala Asp Ala Thr Phe Thr Tyr Arg Pro Ser Val Pro
            100                 105                 110

Ala His Arg Ala Arg Glu Ser Pro Leu Ser Ser Asp Ala Ile Phe
        115                 120                 125

Lys Gln Ser His Ala Gly Leu Phe Asn Leu Cys Val Val Leu Ile
    130                 135                 140

Ala Val Asn Ser Arg Leu Ile Ile Glu Asn Leu Met Lys Ser His Ala
145                 150                 155                 160

Gly Leu Phe Asn Leu Cys Val Val Leu Ile Ala Val Asn Ser Arg
            165                 170                 175

Leu Ile Ile Glu Asn Leu Met Lys Tyr Gly Trp Leu Ile Arg Thr Asp
            180                 185                 190

Phe Trp Phe Ser Ser Arg Ser Leu Arg Asp Trp Pro Leu Phe Met Cys
            195                 200                 205

Cys Ile Ser Leu Ser Ile Phe Pro Leu Ala Ala Phe Thr Val Glu Lys
            210                 215                 220

Leu Val Leu Gln Lys Tyr Ile Ser Glu Pro Val Val Ile Phe Leu His
225                 230                 235                 240

Ile Ile Ile Thr Met Thr Glu Val Leu Tyr Pro Val Tyr Val Thr Leu
                245                 250                 255

Arg Cys Asp Ser Ala Phe Leu Ser Gly Val Thr Leu Met Leu Leu Thr
            260                 265                 270

Cys Ile Val Trp Leu Lys Leu Val Ser Tyr Ala His Thr Ser Tyr Asp
            275                 280                 285

Ile Arg Ser Leu Ala Asn Ala Ala Asp Lys Ala Asn Pro Glu Val Ser
        290                 295                 300

Tyr Tyr Val Ser Leu Lys Ser Leu Ala Tyr Phe Met Val Ala Pro Thr
305                 310                 315                 320

Leu Cys Tyr Gln Pro Ser Tyr Pro Arg Ser Ala Cys Ile Arg Lys Gly
            325                 330                 335

Trp Val Ala Arg Gln Phe Ala Lys Leu Val Ile Phe Thr Gly Phe Met
            340                 345                 350

Gly Phe Ile Ile Glu Gln Tyr Ile Asn Pro Ile Val Arg Asn Ser Lys
            355                 360                 365

His Pro Leu Lys Gly Asp Leu Leu Tyr Ala Ile Glu Arg Val Leu Lys
    370                 375                 380

Leu Ser Val Pro Asn Leu Tyr Val Trp Leu Cys Met Phe Tyr Cys Phe
385                 390                 395                 400

Phe His Leu Trp Leu Asn Ile Leu Ala Glu Leu Leu Cys Phe Gly Asp
            405                 410                 415

Arg Glu Phe Tyr Lys Asp Trp Trp Asn Ala Lys Ser Val Gly Asp Tyr
            420                 425                 430

Trp Arg Met Trp Asn Met Pro Val His Lys Trp Met Val Arg His Ile
            435                 440                 445

Tyr Phe Pro Cys Leu Arg Ser Lys Ile Pro Lys Thr Leu Ala Ile Ile
    450                 455                 460

Ile Ala Phe Leu Val Ser Ala Val Phe His Glu Leu Cys Ile Ala Val
465                 470                 475                 480

Pro Cys Arg Leu Phe Lys Leu Trp Ala Phe Leu Gly Ile Met Phe Gln
            485                 490                 495

Val Pro Leu Val Phe Ile Thr Asn Tyr Leu Gln Glu Arg Phe Gly Ser
            500                 505                 510
```

```
-continued

Thr Val Gly Asn Met Ile Phe Trp Phe Ile Phe Cys Ile Phe Gly Gln
        515                 520                 525

Pro Met Cys Val Leu Leu Tyr Tyr His Asp Leu Met Asn Arg Lys Gly
530                 535                 540

Ser Met Ser
545

<210> SEQ ID NO 26
<211> LENGTH: 11
<212> TYPE: PRT
<213> ORGANISM: Arabidopsis thaliana
<220> FEATURE:
<221> NAME/KEY: misc_feature
<222> LOCATION: (4)..(5)
<223> OTHER INFORMATION: the Xaa at positions 4 and 5 may be any amino
      acid
<220> FEATURE:
<221> NAME/KEY: misc_feature
<222> LOCATION: (8)..(8)
<223> OTHER INFORMATION: the Xaa at position 8 may be any amino acid
<220> FEATURE:
<221> NAME/KEY: misc_feature
<222> LOCATION: (10)..(10)
<223> OTHER INFORMATION: the Xaa at position 10 may be any amino acid

<400> SEQUENCE: 26

His Lys Trp Xaa Xaa Arg His Xaa Tyr Xaa Pro
 1               5                  10
```